(12) United States Patent
Tarczynski et al.

(10) Patent No.: US 7,038,109 B1
(45) Date of Patent: May 2, 2006

(54) ENZYMATIC METHODS FOR MODULATING THE LEVELS OF ORGANIC SULFUR COMPOUNDS IN PLANTS

(75) Inventors: Mitchell C. Tarczynski, West Des Moines, IA (US); Changjiang Li, Urbandale, IA (US); Bo Shen, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 246 days.

(21) Appl. No.: 10/108,739

(22) Filed: Mar. 29, 2002

Related U.S. Application Data

(60) Provisional application No. 60/367,333, filed on Mar. 29, 2001.

(51) Int. Cl.
*C12N 15/82* (2006.01)
*A01H 5/00* (2006.01)
*A01H 5/10* (2006.01)

(52) U.S. Cl. .................. 800/278; 800/298; 800/287; 800/320.1; 435/468

(58) Field of Classification Search ................ 800/278, 800/298, 287, 320.1; 435/468, 419
See application file for complete search history.

(56) References Cited

U.S. PATENT DOCUMENTS

| | | | |
|---|---|---|---|
| 5,912,414 A | 6/1999 | Falco et al. | |
| 5,936,140 A | 8/1999 | Beach | |
| 6,080,913 A | 6/2000 | Tarczynski et al. | |
| 6,127,600 A | 10/2000 | Beach et al. | |
| 6,169,232 B1 | 1/2001 | Hey et al. | |
| 6,608,239 B1 | 8/2003 | Hesse et al. | |

FOREIGN PATENT DOCUMENTS

| | | |
|---|---|---|
| WO | WO 97/41239 | 11/1997 |
| WO | WO 00/04161 | 1/2000 |
| WO | WO 00/36127 | 6/2000 |
| WO | WO 00/49165 | 8/2000 |
| WO | WO 01/75130 A1 | 10/2001 |
| WO | WO 01/94394 A2 * | 12/2001 |

OTHER PUBLICATIONS

Kim et al (2002, Plant Physiology 198:95-107).*
Wirtz et al (2003, Amino Acids (Vienna) 24 (1-2):195-203).*
Schwenn, et al., 1988, *ArchMicrobiol*, 150: 313-319, "Yeast PAPS Reductase: Properties and Requirements of the Purified Enzyme", Ruhr Universitat Bochumm Germany.
Krone, et al., 1991, *Mol. Gen. Genet*, 225: 314-319, "Characterisation of the Gene cysH and of its Product Phospho-adenylylsulphate reductase from *Escherichia coli*", Ruhr University Bochum, Germany.
Guiterrez-Marcos, et al., 1996, *Proc. Natl. Acad. Sci. USA*, 93: 13377-13382, "Three members of a novel small gene family from *Arabidopsis thaliana* able to complement functionally an *Escherichia coli* mutant defective in PAPS reductase activity encode proteins with a yhioredoxin-like domain and "APS reductase" activity", University of St. Andrews, United Kingdom.
Setya, et al., 1996, *Proc. Natl. Acad. Sci. USA*, 93: 13383-13388, "Sulfate Reduction in Higher Plants: Molecular Evidence for a Novel 5'-adenylylsufate Reductase", Rutgers University, New Brunswick, NJ.
Azevedo, et al, 1997, *Phytochemistry*, 46(3): 395-419, "The Biosynthesis and Metabolism of the Aspartate Derived Amino Acids in Higher Plants", Elsevier Science Ltd., Great Britain.
R. Hell, 1997, *Planta*, 202: 138-148, "Molecular Physiology of Plant Sulfur Metabolism", Ruhr-Universitat Bochum, Germany.
Bick, et al., 1998, *Proc. Natl. Acad. Sci, USA*, 95:8404-8409, "Glutaredoxin Function for the Carboxyl-Terminal Domain of the Plant-Type 5' adenylylsulfate reductase", Rutgers University, New Brunswick, NJ and Harvard Medical School, Boston, MA.
Korch, C., et al., 1991, *Mol. Gen. Genet.*, 229: 96-108, "Cloning, Nucleotide Sequence, and Regulation of MET14, the Gene Encoding the APS Kinase of *Saccharomyces cerevisiae*".
Jain, A., et al., 1994, *Plant Physiol*, 105: 771-772, "A cDNA Clone 5'-Adenylylphosphosulfate Kinase from *Arabidopsis thaliana*".
Kim, J., et al., 1996, *Plant Molecular Biology*, 32: 1117-1124, "Cloning and Analysis of the Gene for Cystathionine γ-synthase from *Arabidopsis thaliana*".

(Continued)

*Primary Examiner*—David H. Kruse
*Assistant Examiner*—Stuart F. Baum
(74) *Attorney, Agent, or Firm*—Kathryn K. Lappegard; Pioneer Hi-Bred International, Inc.

(57) ABSTRACT

Methods for modulating levels of at least one organic sulfur compound in plants are provided. Also provided are plants and seeds produced by the methods. The methods comprise stably transforming a plant with a DNA construct encoding a cystathionine gamma synthase enzyme, a serine acetyl transferase enzyme and/or other sulfur assimilating enzymes capable of altering the level of at least one organic sulfur compound.

15 Claims, 7 Drawing Sheets

OTHER PUBLICATIONS

Brunold, C., et al., 1997, *Progress in Botany*, 58(58): 164-186, "Regulation of Sulfur Metabolism in Plants: First Molecular Approaches", Fortschritte Der Botanik, De Springer, Berlin.

Lee, S., et al., 1998, *Biochemical and Biophysical Research Communications*, 247: 171-175, "APS Kinas from *Arabidopsis thaliana*: Genomic Organization, Expression, and Kinetic Analysis of the Recombinant Enzyme".

Bick, J., et al., 1998, *Current Opinion in Plant Biology*, 1(3): 240-244, "Plant Sulfur Metabolism—The Reduction of Sulfate to Sulfite", GB Quandrant Subscription Services.

Suter, M., et al., 2000, *The Journal of Biological Chemistry*, 275(2): 930-936, "Adenosine 5'-Phosphosulfate Sulfotransferase and Adenosine 5'-Phosphosulfate Reductase Are Identical Enzymes".

\* cited by examiner

SEQUENCE LISTING

```
<160> NUMBER OF SEQ ID NOS: 4

<210> SEQ ID NO 1
<211> LENGTH: 927
<212> TYPE: DNA
<213> ORGANISM: Zea mays
<220> FEATURE:
<221> NAME/KEY: CDS
<222> LOCATION: (1)...(925)

<400> SEQUENCE: 1 atg acg gcc ggg cag ctt ctg cgc acc gag cca tca gcc cag ccc cag      48
Met Thr Ala Gly Gln Leu Leu Arg Thr Glu Pro Ser Ala Gln Pro Gln
 1               5                  10                  15 cgg gtg cgc cac agc acc ccg ccg gcg gca ctc caa gca gac atc gtg      96
Arg Val Arg His Ser Thr Pro Pro Ala Ala Leu Gln Ala Asp Ile Val
             20                  25                  30 ccg tcg tac ccg ccg ccc gag tcg gac ggt gac gag tcg tgg gtc tgg     144
Pro Ser Tyr Pro Pro Pro Glu Ser Asp Gly Asp Glu Ser Trp Val Trp
         35                  40                  45 tcc cag atc aag gcg gag gcg cgg cgc gac gcg gac gcg gag ccg gcg     192
Ser Gln Ile Lys Ala Glu Ala Arg Arg Asp Ala Asp Ala Glu Pro Ala
     50                  55                  60 ctg gcc tcc ttc ctc tac gcg acg gtg ctg tcg cac gcg tcc ctg gac     240
Leu Ala Ser Phe Leu Tyr Ala Thr Val Leu Ser His Ala Ser Leu Asp
 65                  70                  75                  80 cgg tcc ctg gcc ttc cac ctg gcc aac aag ctg tgc tcc tcc acg ctg     288
Arg Ser Leu Ala Phe His Leu Ala Asn Lys Leu Cys Ser Ser Thr Leu
                 85                  90                  95 ctg tcg acg ctc tct aac gac ctc ttc gtg gcg tcg ctc gcg gag cac     336
Leu Ser Thr Leu Ser Asn Asp Leu Phe Val Ala Ser Leu Ala Glu His
            100                 105                 110 ccg tcg tcc gcg cgg cgg cgg tgg cga cct gat cgc cgc gcg gtc gcg     384
Pro Ser Ser Ala Arg Arg Arg Trp Arg Pro Asp Arg Arg Ala Val Ala
        115                 120                 125 gga ccc ggc tgc gcg ggc ttc gcg cac tgc ctc ctc aac tac aag ggg     432
Gly Pro Gly Cys Ala Gly Phe Ala His Cys Leu Leu Asn Tyr Lys Gly
    130                 135                 140 ttc ctg gcc gtg cag gcg cac cgc gtg gcg cac gtg ctg tgg gcg cag     480
Phe Leu Ala Val Gln Ala His Arg Val Ala His Val Leu Trp Ala Gln
145                 150                 155                 160 ggc cgg cgc gcg ctg gcg ctg gcg ctc cag tcc cgc gtc gcc gag gtc     528
Gly Arg Arg Ala Leu Ala Leu Ala Leu Gln Ser Arg Val Ala Glu Val
                165                 170                 175 ttc gcc gtg gac atc cac ccg gcc gcc acc gtc ggc agg ggc atc ctg     576
Phe Ala Val Asp Ile His Pro Ala Ala Thr Val Gly Arg Gly Ile Leu
            180                 185                 190 ctc gac cac gcc acg ggc gtc gtc gtc ggg gag acg gcc gtc gtg ggc     624
Leu Asp His Ala Thr Gly Val Val Val Gly Glu Thr Ala Val Val Gly
        195                 200                 205
```

-continued

```
gac aac gtc tcc ata ctc cac cac gtg acg ttg gcg gca ccg gca agg    672
Asp Asn Val Ser Ile Leu His His Val Thr Leu Ala Ala Pro Ala Arg
    210                 215                 220 cgt tgg cga ccg gca ccc caa gat cgg gac ggc gtg ctc atc ggc gcc    720
Arg Trp Arg Pro Ala Pro Gln Asp Arg Asp Gly Val Leu Ile Gly Ala
225                 230                 235                 240 ggc gcg acc gtc ctc gga aac gtc agg atc ggc gcc ggc gcc aag gtc    768
Gly Ala Thr Val Leu Gly Asn Val Arg Ile Gly Ala Gly Ala Lys Val
                245                 250                 255 ggc gcc ggg tcc gtc gtg ctc atc gac gtg ccg ccc agg agc acc gcc    816
Gly Ala Gly Ser Val Val Leu Ile Asp Val Pro Pro Arg Ser Thr Ala
            260                 265                 270 gtg ggg aac ccc gcc agg ctg atc ggc ggg aag aag ggc gag gag gtg    864
Val Gly Asn Pro Ala Arg Leu Ile Gly Gly Lys Lys Gly Glu Glu Val
        275                 280                 285 atg ccg ggg gag tcc atg gac cac acc tcc ttc ata cag cag tgg tcg    912
Met Pro Gly Glu Ser Met Asp His Thr Ser Phe Ile Gln Gln Trp Ser
    290                 295                 300 gac tac atc att t ga                                               927
Asp Tyr Ile Ile
305
```

<210> SEQ ID NO 2
<211> LENGTH: 308
<212> TYPE: PRT
<213> ORGANISM: Zea mays

<400> SEQUENCE: 2

```
Met Thr Ala Gly Gln Leu Leu Arg Thr Glu Pro Ser Ala Gln Pro Gln
1               5                   10                  15

Arg Val Arg His Ser Thr Pro Pro Ala Ala Leu Gln Ala Asp Ile Val
            20                  25                  30

Pro Ser Tyr Pro Pro Glu Ser Asp Gly Asp Glu Ser Trp Val Trp
        35                  40                  45

Ser Gln Ile Lys Ala Glu Ala Arg Arg Asp Ala Asp Ala Glu Pro Ala
    50                  55                  60

Leu Ala Ser Phe Leu Tyr Ala Thr Val Leu Ser His Ala Ser Leu Asp
65                  70                  75                  80

Arg Ser Leu Ala Phe His Leu Ala Asn Lys Leu Cys Ser Ser Thr Leu
                85                  90                  95

Leu Ser Thr Leu Ser Asn Asp Leu Phe Val Ala Ser Leu Ala Glu His
            100                 105                 110

Pro Ser Ser Ala Arg Arg Arg Trp Arg Pro Asp Arg Arg Ala Val Ala
        115                 120                 125

Gly Pro Gly Cys Ala Gly Phe Ala His Cys Leu Leu Asn Tyr Lys Gly
    130                 135                 140

Phe Leu Ala Val Gln Ala His Arg Val Ala His Val Leu Trp Ala Gln
145                 150                 155                 160

Gly Arg Arg Ala Leu Ala Leu Ala Leu Gln Ser Arg Val Ala Glu Val
                165                 170                 175

Phe Ala Val Asp Ile His Pro Ala Ala Thr Val Gly Arg Gly Ile Leu
            180                 185                 190

Leu Asp His Ala Thr Gly Val Val Val Gly Glu Thr Ala Val Val Gly
        195                 200                 205

Asp Asn Val Ser Ile Leu His His Val Thr Leu Ala Ala Pro Ala Arg
    210                 215                 220

Arg Trp Arg Pro Ala Pro Gln Asp Arg Asp Gly Val Leu Ile Gly Ala
```

```
                225                 230                 235                 240
        Gly Ala Thr Val Leu Gly Asn Val Arg Ile Gly Ala Gly Ala Lys Val
                        245                 250                 255

Gly Ala Gly Ser Val Val Leu Ile Asp Val Pro Arg Ser Thr Ala
                    260                 265                 270

Val Gly Asn Pro Ala Arg Leu Ile Gly Gly Lys Lys Gly Glu Val
                    275                 280                 285

Met Pro Gly Glu Ser Met Asp His Thr Ser Phe Ile Gln Gln Trp Ser
                290                 295                 300

Asp Tyr Ile Ile
        305

<210> SEQ ID NO 3
<211> LENGTH: 1470
<212> TYPE: DNA
<213> ORGANISM: Zea mays
<220> FEATURE:
<221> NAME/KEY: CDS
<222> LOCATION: (1)...(1468)

<400> SEQUENCE: 3 atg gcg aca cag gcc gct ttc ctc gca ggg ttc tcg cag ctc gcc gcg      48
Met Ala Thr Gln Ala Ala Phe Leu Ala Gly Phe Ser Gln Leu Ala Ala
 1               5                  10                  15 cag ccg ggc cgc gac cgc gcc gtg gcg gtg gcg gtg gcg ccg gcg ccg      96
Gln Pro Gly Arg Asp Arg Ala Val Ala Val Ala Val Ala Pro Ala Pro
                20                  25                  30 ggc ccg gcc cgg gtg gcc gtt gcg gcg gtg ggt agc gcc aag ttg ggc     144
Gly Pro Ala Arg Val Ala Val Ala Ala Val Gly Ser Ala Lys Leu Gly
            35                  40                  45 gtg aag gcg ggg acg tcc agg acc gcg gcg gtg gcg cgc ctc ggg gtg     192
Val Lys Ala Gly Thr Ser Arg Thr Ala Ala Val Ala Arg Leu Gly Val
         50                  55                  60 cgg tgc cgg gcc agc ctg atc gag ccc gac ggc ggg cgg ctg gtg gac     240
Arg Cys Arg Ala Ser Leu Ile Glu Pro Asp Gly Gly Arg Leu Val Asp
 65                  70                  75                  80 ctg gtg gcg ccc gag gag ggc ggg cgg cgc gcg gcg ctg cgg cgg gag     288
Leu Val Ala Pro Glu Glu Gly Gly Arg Arg Ala Ala Leu Arg Arg Glu
                 85                  90                  95 gcg gcg gag ctg ccg cac cgg ctg cgc ttg ggc cgc gtc gac aag gaa     336
Ala Ala Glu Leu Pro His Arg Leu Arg Leu Gly Arg Val Asp Lys Glu
                100                 105                 110 tgg gtc cac gtc ctc agc gaa ggg tgg gcg agc ccg ctg caa ggg ttc     384
Trp Val His Val Leu Ser Glu Gly Trp Ala Ser Pro Leu Gln Gly Phe
            115                 120                 125 atg cgc gag cat gag ttc ctc caa gca ctt cat ttc aat gcc atc cgc     432
Met Arg Glu His Glu Phe Leu Gln Ala Leu His Phe Asn Ala Ile Arg
        130                 135                 140 ggc cag gat ggc agg atg gtc aac atg tcc gtc ccc atc gtg ctc tct     480
Gly Gln Asp Gly Arg Met Val Asn Met Ser Val Pro Ile Val Leu Ser
145                 150                 155                 160 gtc ggg gac gca cag cga agg gcc atc cag gcc gac ggc gcc acg cgc     528
Val Gly Asp Ala Gln Arg Arg Ala Ile Gln Ala Asp Gly Ala Thr Arg
                165                 170                 175 gtc gcg ctc gtt gac gag cgc gac cgc ccc atc gcc gtc ctc agc gac     576
Val Ala Leu Val Asp Glu Arg Asp Arg Pro Ile Ala Val Leu Ser Asp
            180                 185                 190 att gag atc tat aag cat aat aag gaa gaa agg gta gca cgg aca tgg     624
Ile Glu Ile Tyr Lys His Asn Lys Glu Glu Arg Val Ala Arg Thr Trp
        195                 200                 205
```

```
ggg aca act gca cct gga tta cct tat gtc gag gag gca att acc aat    672
Gly Thr Thr Ala Pro Gly Leu Pro Tyr Val Glu Glu Ala Ile Thr Asn
    210                 215                 220 gct ggt gac tgg ttg gtt ggt ggg gac ttg gag gtt ata gaa cca atc    720
Ala Gly Asp Trp Leu Val Gly Gly Asp Leu Glu Val Ile Glu Pro Ile
225                 230                 235                 240 aag tac aac gat ggt cta gat cag tat cgc ctg tct cca gca cag ctg    768
Lys Tyr Asn Asp Gly Leu Asp Gln Tyr Arg Leu Ser Pro Ala Gln Leu
                245                 250                 255 cgt gaa gag ttt gcc agg cgc aat gct gat gca gta ttt gcc ttt cag    816
Arg Glu Glu Phe Ala Arg Arg Asn Ala Asp Ala Val Phe Ala Phe Gln
            260                 265                 270 ctt cgc aat cct gta cac aat ggg cat gct ctt ctt atg acc gac aca    864
Leu Arg Asn Pro Val His Asn Gly His Ala Leu Leu Met Thr Asp Thr
        275                 280                 285 cgc aaa cgt ctc ctt gag atg ggt tat aaa aac cct gtt ctt ctg ctc    912
Arg Lys Arg Leu Leu Glu Met Gly Tyr Lys Asn Pro Val Leu Leu Leu
    290                 295                 300 cat cca ctg gga gga ttc aca aaa gca gat gat gtg cct ctt agt tgg    960
His Pro Leu Gly Gly Phe Thr Lys Ala Asp Asp Val Pro Leu Ser Trp
305                 310                 315                 320 aga atg aag caa cat gag aag gtt ctt gag gaa ggt gtc ctc aac cca   1008
Arg Met Lys Gln His Glu Lys Val Leu Glu Glu Gly Val Leu Asn Pro
                325                 330                 335 gaa tca act gtt gtt gcg atc ttt ccc tct cca atg cat tat gct ggg   1056
Glu Ser Thr Val Val Ala Ile Phe Pro Ser Pro Met His Tyr Ala Gly
            340                 345                 350 cca act gag gtg cag tgg cat gct aag gct cgt att aat gct ggt gca   1104
Pro Thr Glu Val Gln Trp His Ala Lys Ala Arg Ile Asn Ala Gly Ala
        355                 360                 365 aat ttc tat att gtt gga agg gat cct gct ggt atg agc cat ccc acg   1152
Asn Phe Tyr Ile Val Gly Arg Asp Pro Ala Gly Met Ser His Pro Thr
    370                 375                 380 gag aaa agg gac ctc tat gat gct gac cac ggg aag aag gtt ttg agc   1200
Glu Lys Arg Asp Leu Tyr Asp Ala Asp His Gly Lys Lys Val Leu Ser
385                 390                 395                 400 atg gct cct ggc ctc gag agg ctc aac atc ctt cct ttc aag gtg gct   1248
Met Ala Pro Gly Leu Glu Arg Leu Asn Ile Leu Pro Phe Lys Val Ala
                405                 410                 415 gca tat gac aca aag caa aag aaa atg gat ttc ttc gat cca tca agg   1296
Ala Tyr Asp Thr Lys Gln Lys Lys Met Asp Phe Phe Asp Pro Ser Arg
            420                 425                 430 aaa gat gat ttc ctc ttc atc tct ggc aca aag atg cgc act ctt gcc   1344
Lys Asp Asp Phe Leu Phe Ile Ser Gly Thr Lys Met Arg Thr Leu Ala
        435                 440                 445 aag aac cgc gag agt ccc ccg gat ggt ttt atg tgc ccg ggt ggc tgg   1392
Lys Asn Arg Glu Ser Pro Pro Asp Gly Phe Met Cys Pro Gly Gly Trp
    450                 455                 460 aaa gtg ctc gtt gaa tac tat gac agc ttg gtg cca tcc gag ggc agc   1440
Lys Val Leu Val Glu Tyr Tyr Asp Ser Leu Val Pro Ser Glu Gly Ser
465                 470                 475                 480 agc aag ctg cgc gag cca gtt gca gcc t ga                          1470
Ser Lys Leu Arg Glu Pro Val Ala Ala
                485

<210> SEQ ID NO 4
<211> LENGTH: 489
<212> TYPE: PRT
<213> ORGANISM: Zea mays
```

```
<400> SEQUENCE: 4

Met Ala Thr Gln Ala Ala Phe Leu Ala Gly Phe Ser Gln Leu Ala Ala
 1               5                  10                  15

Gln Pro Gly Arg Asp Arg Ala Val Ala Val Ala Pro Ala Pro
            20                  25                  30

Gly Pro Ala Arg Val Ala Val Ala Val Gly Ser Ala Lys Leu Gly
                35                  40              45

Val Lys Ala Gly Thr Ser Arg Thr Ala Val Ala Arg Leu Gly Val
 50                  55                  60

Arg Cys Arg Ala Ser Leu Ile Glu Pro Asp Gly Arg Leu Val Asp
 65                  70                  75                  80

Leu Val Ala Pro Glu Glu Gly Arg Arg Ala Ala Leu Arg Arg Glu
                85                  90                  95

Ala Ala Glu Leu Pro His Arg Leu Arg Leu Gly Arg Val Asp Lys Glu
                100                 105                 110

Trp Val His Val Leu Ser Glu Gly Trp Ala Ser Pro Leu Gln Gly Phe
                115                 120                 125

Met Arg Glu His Glu Phe Leu Gln Ala Leu His Phe Asn Ala Ile Arg
130                 135                 140

Gly Gln Asp Gly Arg Met Val Asn Met Ser Val Pro Ile Val Leu Ser
145                 150                 155                 160

Val Gly Asp Ala Gln Arg Ala Ile Gln Ala Asp Gly Ala Thr Arg
                165                 170                 175

Val Ala Leu Val Asp Glu Arg Asp Arg Pro Ile Ala Val Leu Ser Asp
                180                 185                 190

Ile Glu Ile Tyr Lys His Asn Lys Glu Glu Arg Val Ala Arg Thr Trp
                195                 200                 205

Gly Thr Thr Ala Pro Gly Leu Pro Tyr Val Glu Glu Ala Ile Thr Asn
                210                 215                 220

Ala Gly Asp Trp Leu Val Gly Gly Asp Leu Glu Val Ile Glu Pro Ile
225                 230                 235                 240

Lys Tyr Asn Asp Gly Leu Asp Gln Tyr Arg Leu Ser Pro Ala Gln Leu
                245                 250                 255

Arg Glu Glu Phe Ala Arg Arg Asn Ala Asp Ala Val Phe Ala Phe Gln
                260                 265                 270

Leu Arg Asn Pro Val His Asn Gly His Ala Leu Leu Met Thr Asp Thr
                275                 280                 285

Arg Lys Arg Leu Leu Glu Met Gly Tyr Lys Asn Pro Val Leu Leu Leu
                290                 295                 300

His Pro Leu Gly Gly Phe Thr Lys Ala Asp Asp Val Pro Leu Ser Trp
305                 310                 315                 320

Arg Met Lys Gln His Glu Lys Val Leu Glu Glu Gly Val Leu Asn Pro
                325                 330                 335

Glu Ser Thr Val Val Ala Ile Phe Pro Ser Pro Met His Tyr Ala Gly
                340                 345                 350

Pro Thr Glu Val Gln Trp His Ala Lys Ala Arg Ile Asn Ala Gly Ala
                355                 360                 365

Asn Phe Tyr Ile Val Gly Arg Asp Pro Ala Gly Met Ser His Pro Thr
                370                 375                 380

Glu Lys Arg Asp Leu Tyr Asp Ala Asp His Gly Lys Lys Val Leu Ser
385                 390                 395                 400

Met Ala Pro Gly Leu Glu Arg Leu Asn Ile Leu Pro Phe Lys Val Ala
                405                 410                 415
```

-continued

```
Ala Tyr Asp Thr Lys Gln Lys Lys Met Asp Phe Phe Asp Pro Ser Arg
            420             425             430

Lys Asp Asp Phe Leu Phe Ile Ser Gly Thr Lys Met Arg Thr Leu Ala
        435             440             445

Lys Asn Arg Glu Ser Pro Pro Asp Gly Phe Met Cys Pro Gly Gly Trp
    450             455             460

Lys Val Leu Val Glu Tyr Tyr Asp Ser Leu Val Pro Ser Glu Gly Ser
465             470             475             480

Ser Lys Leu Arg Glu Pro Val Ala Ala
                485
```

US 7,038,109 B1

ENZYMATIC METHODS FOR MODULATING THE LEVELS OF ORGANIC SULFUR COMPOUNDS IN PLANTS

CROSS-REFERENCE TO RELATED APPLICATIONS

This application claims priority to and the benefit of U.S. Provisional Application Ser. No. 60/367,333 filed Mar. 29, 2001 which is herein incorporated by reference.

FIELD OF THE INVENTION

The invention relates to the genetic manipulation of plants, particularly to enzymatic methods for altering sulfur metabolism in plants and plant seeds.

BACKGROUND OF THE INVENTION

Sulfur in its reduced form plays an important role in plant metabolism, being involved in the biosynthesis of a wide range of primary and secondary sulfur-containing metabolites. In plants, sulfur metabolism includes the uptake of sulfate from the environment, assimilation into organic compounds, and channeling into proteins and secondary substances.

Plants and microorganisms are able to reduce sulfate to sulfide for synthesis of the thiol group of cysteine. The first step is the activation of sulfate by ATP sulfurylase, forming 5'-adenylylsulfate (APS). APS reductase acts upon APS to generate sulfite, and sulfite reductase converts this sulfite to hydrogen sulfide. This hydrogen sulfide provides the thiol group to cysteine, while the carbon portion of cysteine comes from the serine branch of the pathway. In this branch, serine is converted to O-acetylserine by serine acetyltransferase. Cysteine synthase then catalyzes the reaction of O-acetylserine and hydrogen sulfide to form cysteine.

Cystathionine gamma synthase catalyzes the reaction between O-phosphohomoserine and cysteine, wherein the cysteine donates a thiol group to O-phosphohomoserine, thereby forming cystathionine.

Methionine, and sulfur-containing vitamins such as biotin or thiamine are essential in human nutrition. Sulfur-mediated functions include electron transport in Fe/S-clusters, structural and regulatory roles via protein disulfide bridges, and catalytic centers. Additionally, secondary sulfur compounds include signaling molecules, anti-carcinogens and atmospheric compounds. See Hell (1997) *Planta* 202:138.

Often plant protein is deficient in the sulfur amino acids, especially methionine, as well as other essential amino acids such as lysine and tryptophan. As a result, diets must be supplemented with these amino acids in order to provide a balanced diet. A goal of plant breeding has been to increase the amount of sulfur amino acids present in the seed.

A number of methods have been described for increasing sulfur amino acid content of plants. Some of these methods provide for the overexpression of a high methionine seed storage protein, which entails overexpressing the seed storage protein in a transformed plant. Other methods have attempted seed specific expression of synthetic enzymes in the methionine pathway. Still other methods have focused on enzymatic modification of amino acids and capturing these amino acids in transgenic seed storage proteins. However, these methods have met with limited success. There is therefore a need for an effective and direct method of producing significant levels of the sulfur amino acids in plants and plant seeds.

SUMMARY OF THE INVENTION

An object of the present invention is to provide methods for increasing the nutritional value of plants.

Another object of the present invention is to provide plants and plant parts having increased nutritional value.

Another object of the present invention is to provide plants and plant parts having increased levels of organic sulfur compounds.

Another object of the present invention is to provide plants and plant parts having increased levels of methionine.

Another object of the present invention is to provide plants and plant parts having increased levels of cysteine.

In accordance with the present invention, methods for modulating the level of at least one organic sulfur compound in plants are provided. Also provided are plants, plant tissues, plant seeds and plant cells produced by the methods. The methods comprise stably transforming a plant with a DNA construct encoding a cystathionine gamma synthase and/or serine acetyl transferase enzyme.

DETAILED DESCRIPTION OF THE INVENTION

Figure 1:
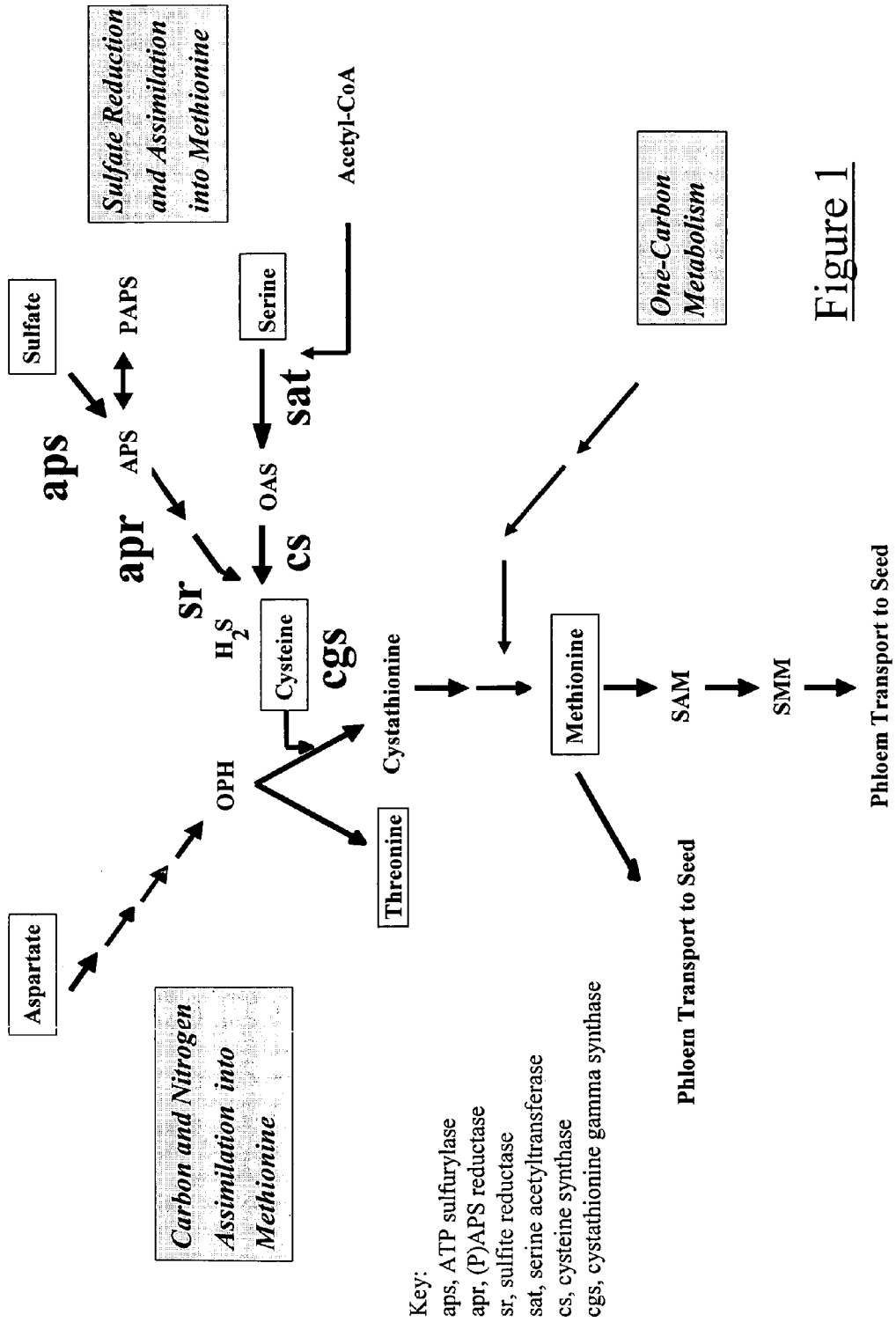
FIG. 1 sets forth the biosynthesis for the organic sulfur compounds cysteine and methionine with the proposed modifications of the invention.

In accordance with the subject invention, compositions and methods for modulating the biosynthesis of organic sulfur compounds in plants, particularly sulfur amino acids, more particularly cysteine and methionine, are provided. The methods involve transforming a monoctyledonous plant with one or more nucleic acid(s) encoding cystathionine gamma synthase or serine acetyl transferase. The plant may also comprise one or more additional nucleic acid(s) selected from nucleic acids encoding enzymes involved in amino acid biosynthesis and sulfate reduction.

Previous attempts to modulate the biosynthesis of organic sulfur compounds through enzymatic modification has focused upon the enzymatic modification occurring in the plant seed. This is because the plant seed is the desired source for the modulated organic sulfur compound. Surprisingly, Applicants have discovered that modulated expression of cystathionine gamma synthase and/or serine acetyltransferase need not occur in a monocot plant seed in order to modulate the biosynthesis of organic sulfur compounds in the plant seed. Through non-seed specific enzymatic modulation of cystathionine gamma synthase or serine acetyl transferase, Applicants have increased the levels of methionine in a monocot seed beyond those achieved through seed specific enzyme modification. Perhaps most surprisingly, such increase in the seed was accomplished without transgenic modification of the plant to increase the expression of a seed storage protein containing the desired amino acids.

By "organic sulfur compounds" is intended a compounds such as cysteine, cystathionine, methionine, glutathione, dimethylsulfoniopropionate (DMSP), SMM (Vitamin U), biotin, SAM, Thiamine pyrophosphate (Vitamin B-1), Coenzyme A and sulfur containing phytoalexins.

Sulfate reduction occurs in both roots and shoots of plants. Most of the sulfur transported in the xylem to the leaves is in non-reduced $SO_4^{2-}$. Some transport back to roots and other parts of the plant occurs through phloem, and both free $SO_4^{2-}$ and organic sulfur compounds are transported. In leaves, the process of sulfate reduction occurs in chloroplasts. In roots, most or all of the process occurs in proplastids.

Therefore, a preferred embodiment of the present invention is to provide cystathionine gamma synthase and/or serine acetyl transferase expression in the non-seed tissues of the plant where sulfate reduction is most active. This can be accomplished through tissue specific expression of these enzymes in non-seed tissue, such as leaves, roots or shoots or by constitutive expression of these enzymes. Constitutive expression will result in expression in both seed and non-seed tissue. Other methods can be used for increasing the activity of the cystathionine gamma synthase and/or serine acetyl transferase, such as protein engineering or DNA shuffling.

Other nucleic acids encoding enzymes involved in sulfate reduction or organic sulfur compound biosynthesis, such as cysteine and methionine biosynthesis, can be utilized to shunt the pathway in particular directions. For example, APS kinase can be down-regulated to increase APS concentration for APS reductase. In the same manner, an increase in methionine can be utilized as a sulfur source for downstream sulfur containing compounds. For example, glutathione is produced by the two step reaction of glutamate+cysteine+ATP→gamma-glutamylcysteine+ADP+Pi, followed by gamma-glutamylcysteine+glycine+ATP→glutathione+ADP+Pi, which reaction is catalyzed by glutathione synthetase. Another example is the series of reactions converting methionine to dimethylsulfoniopropionate (DMSP); the reactions converting methionine to vitamins and co-vitamins such as biotin, SMM (Vitamin U), SAM, Thiamine pyrophosphate (Vitamin B-1) and Coenzyme A; and the series of reactions converting methionine to sulfur containing phytoalexins that serve a pathogen defense function.

Also, antisense constructs for cystathionine gamma synthase and/or serine acetyl transferase can be utilized to direct biosynthesis into a particular product or to stop biosynthesis for the build-up of a particular compound. For example, an antisense construct for cystathionine gamma synthase can be used to shunt reduced sulfur away from methionine production.

Any means for producing a plant comprising the cystathionine gamma synthase or serine acetyl transferase are encompassed by the present invention. Additional nucleic acid(s) of interest can also be used to transform a plant at the same time as the cystathionine gamma synthase and/or serine acetyl transferase (cotransformation). The additional nucleic acid(s) of interest may code for other enzymes in the methionine pathway that will further modify cysteine or methionine levels or downstream sulfur containing compounds such as sulfur containing vitamins. The additional nucleic acid can also be introduced into a plant that has already been transformed with the cystathionine gamma synthase and/or serine acetyl transferase nucleic acid. Alternatively, transformed plants, one expressing the cystathionine gamma synthase and/or serine acetyl transferase and one expressing the additional nucleic acid, can be crossed to bring the nucleic acids together in the same plant. Subsequent crosses or transformations can bring additional sequences together in the plant.

Enzymes involved in cysteine and methionine biosynthesis are known in the art. See, for example, aspartokinase (Masakazu et al. (1992) "Mutant Aspartokinase Gene," Japan Patent 1994062866-A 1 08-MAR-1994, Accession No. E06825; Omori et al. (1993) *J. Bacteriol.* 175(3): 785–794; Accession No. X60821; Moriya et al. (1995) Japan Patent 1997070291-A 13 18-MAR-1997; Accession No. E12770); aspartate semialdehyde dehydrogenase (Calzada, F. R. A., Direct Submission, Centro Nacional de Investigaciones Cientificas, Avenida 25 esq. 158 reparto Cubanacan, Playa Ciudad de la Habana, Codigo Postal 6990, CUBA (1997), Accession No. Y15281; Daniel et al. (1993) *J. Mol. Biol.* 232 (2):468–483; Accession No. Z22554; Chen et al. (1993) *J. Biol. Chem.*; Accession No. Z22554; Accession No. U90239; Brakhage et al. (1990) *Biochimie* 72(10): 725–734; Accession No. Z75208; Gothel et al. (1997) *Eur. J. Biochem.* 244 (1):59–65; Accession No. Z75208); homoserine kinase (See number two under aspartokinase, Accession No. X60821; Nakabachi et al. (1997) *Insect Biochem. Mol. Biol.* 27:1057–1062; Accession No. AB004856; Ryoichi et al. (1986) Japan Patent 1987232392-A 1 12-OCT-1987 (JP1986076298); Accession No. E01358; Sadao et al. Japan Patent 1993207886-A 4 20-AUG-1993; Accession No. DI 4072); threonine synthase (see number two under aspartokinase, Accession No. X6082; Accession No. Z46263; Rognes, S. E., Direct Submission, Oct. 24, 1994, to University of Oslo, Department of Biology, Blindern, 0316 Norway, Accession No. Z46263; Accession No. L41666; Clepet et al. (1992) *Mol. Microbiol.* 6(21):3109–3119; Accession No. X65033 S50569; Cami, B., Direct Submission, Mar. 11, 1992, Laboratoire de Chimie Bacterienne, Centre Nationale de la Recherche, Scientifique, 31 Chemin I. Aiguier, BP 71 13277 Marseille Cedex, FRANCE, Accession No. X65033 S50569); cystathionine gamma synthase (cystathionine gamma synthase) (Kim and Leustek (1996) "Cloning and analysis of the gene for cystathionine gamma-synthase from *Arabidopsis thaliana*," Plant Mol. Biol. 32 (6), 1117–1124, USA, Accession No. AF069317; Locke et al., Direct Submission, Jun. 3, 1997, AG Biotechnology, Dupont AF Products, PO Box 80402, Wilmington, Del. 19880–0402 USA, maize cystathionine gamma synthase, Accession No. AF007785 and AF007786; rice cystathionine gamma synthase (AF076495); potato cystathionine gamma synthase (AF082891, AF082892, AF144102); soybean cystathionine gamma synthase (AF141602); *arabidopsis* cystathionine gamma synthase (U43709, U83500, X94756, AC027035, AC051630); cystathionine beta lyase (Bork et al. (1997) *Plant Physiol.* 115:864—864; Accession No. AJ001148; Sienko, M., Direct Submission, Jun. 5, 1995, Marzena Sienko, Genetics, Institute of Biochemistry and Biophysics, Pawinskiego 5a, Warsaw 02–106, POLAND, Accession No. U28383; Ravanel et al. (1995) *Plant Mol. Biol.* 29 (4):875–882; Accession No. L40511); methionine synthase (Kurvari et al. (1995) *Plant Mol. Biol.* 29:1235–1252; Accession No. U36197; Ravanel et al. (1998) *Proc. Natl. Acad. Sci. USA* 95(13):7805–7812;

Accession No. U97200; Michalowski et al., Direct Submission, Jan. 12, 1997, Biochemistry, University of Arizona, BioSciences West 513, Tucson, Ariz. 85721 USA, Accession No. U84889; Eichel et al. (1995) *Eur. J. Biochem.* 230 (3):1053–1058; Accession No. X83499); ATP sulfurylase (Murillo et al. (1995) *Arch. Biochem. Biophys.* 323(1): 195–204; Accession No. U06275; Leustek et al. (1994) *Plant Physiol.* 105:897–902; Accession No. U05218; Bolchi et al., Direct Submission, Jul. 28, 1997, Scienze Biochimiche, Viale delle Scienze, Parma, PR 43100 ITALY, Accession No. AF016305; Laue et al. (1994) *J. Bacteriol.* 176:3723–3729; Accession No. L26897; Laeremans et al. Accession No. AJ001223); U.S. patent application Ser. No. 09/346,408 by DuPont entitled, *Sulfate Assimilation Proteins*; soybean ATP sulfurylase (BG156200, BG045264, BG041863, BF009916, BF009045, BE807651, BE804451, BE556220, BE475509, BE473960, BE210444, BE191366, AW458276, AW309791, AW278474, AW277946, AW277743, AW234410), tomato ATP sulfurylase (BF113119, BF096727), rice ATP sulfurylase (AB015204), *brassica juncea* ATP sulfurylase (AJ223498), *brassica oleracea* ATP sulfurylase (AF195511), allium ATP sulfurylase (AF212154), arabidopsis ATP sulfurylase (BE844959, BE039475, AJ012586, U59737, AF198964, AF110407, U59738, AL161539, AP001300, S68202); APS kinase (apk) (Korch et al. (1991) *Mol. Gen. Genet.* 229(1):96–108; Accession No. S55315; Arz et al. (1994) *Biochim. Biophys. Acta* 1218 (3):447–452; Accession No. AF044285; Schiffmann et al. "Isolation of cDNA clones encoding adenosine-5'-phophosulfate-kinase (EC2.7.1.25) from *Catharanthus roseus* (Accession No. AF044285) and an isoform (akn2) from *Arabidopsis* (Accession No. AF043351) (PGR98–116)," *Plant Physiol.* 117 (3):1125 (1998); Accession No. AF044285; Jain et al. (1994) *Plant Physiol.* 105: 771–772; Accession No. U05238; Lee et al. (1998) *Biochem. Biophys. Res. Commun.* 247:171–175; Accession No. U05238); APS reductase (Speich et al. (1994) *Microbiology* 140 (Pt6):1273–1284; Accession No. Z69372; Setya et al. (1996) *Proc. Natl. Acad. Sci. USA* 93(23):13383–1338; Accession No. U56921; Bick et al. (1998) *Proc. Natl. Acad. Sci. USA* 95(14):8404–8409; DuPont patent application, Genes Encoding Sulfate Assimilation Proteins, PCT publication number WO00/04161); PAPS reductase (Krone et al. (1991) *Mol. Gen. Genet.* 225(2):314–319; Accession No. Y07525; Krone et al. (1990) *FEBS Lett.* 260 (1):6–9; Accession No. Y07525; Gutierrez-Marcos et al. (1996) *Proc. Natl. Acad. Sci. USA* 93:13377–13382; Accession No. U53865; Schwenn, J. D., Direct Submission, Jul. 2, 1993, Ruhr-University-Bochum, Fac. Biology, Biochemistry of Plants, Universitaetsstr. 150, D44780 Bochum, GERMANY, Accession No. Z23169; see number five under ATP sulfurylase, Accession No. AJ001223; Bussey et al. (1997) *Nature* 387 (6632 *Suppl.*):103–105; Accession No. U25840 U00094); sulfite reductase (Accession No. Y07525; Accession No. Z23169; Hipp et al. (1997) *Microbiology* 143 (Pt 9):2891–2902; Accession No. U84760; Pott et al. (1998) *Microbiology* 144 (Pt 7):1881–1894; Accession No. U84760; Bork et al. (1998) *Gene* 212 (1):147–153; Accession No. Y10157; Mbeguie-A-Mbeguie et al. Accession No. AF071890; Bruehl et al. (1996) *Biochim. Biophys. Acta* 1295:119–124; Accession No. Z49217; Hummerjohann et al. (1998) *Microbiology* 144 (Pt 5):1375–1386; Accession No. AF026066; serine acetyltransferase (Accession No. X80938; Accession No. D88529 and D88530; Saito et al. (1995)*J. Biol. Chem.* 270 (27): 16321–16326; Accession No. D49535; DuPont patent application, Genes Encoding Sulfate Assimilation Proteins, PCT publication number WO 00/04167; see also arabidopsis serine acetyl transferase (U22964, L78443, X8288, L78444, AF112303, U30298, L42212, U22964, L78443, X82888, Z34888 and X80938), soybean serine acetyl transferase (BF041806, BE802695, AW234818, A1965408, A1495784, A1437954), tomato serine acetyl transferase (BF176520, BF098353), allium serine acetyl transferase (AF212156, AB040502) and cotton serine acetyl transferase (AI725434); cysteine synthase (Hesse et al. (1998) "Isolation of cDNAs encoding cytosolic (Accession No. AF044172) and plastidic (Accession No. AF044173) cysteine synthase isoforms from *Solanum tuberosum* (PGR98–057)," *Plant Physiol.* 116:1604, Accession No. AF044173; Brander et al. (1995) *Plant Physiol.* 108:1748—1748; Accession No. X85803; Topczewski et al. (1997) *Curr. Genet.* 31 (4):348–356; Accession No. U19395); gamma glutamylcysteine synthase (Powles et al. (1996) *Microbiology* 142 (Pt 9):2543–2548; Accession No. U81808 L75931; Accession No. AL031018; EU *Arabidopsis* sequencing project, Direct Submission, Jul. 3, 1998, at the Max-Planck-Institut fuer Biochemie, Am Klopferspitz 18a, D-82152 Martinsried, FRG, Accession No. AL031018); glutathione synthetase (Okumura et al. (1997) *Microbiology* 143 (Pt 9):2883–2890; Accession No. D88540; Inoue et al. (1998) *Biochim. Biophys. Acta* 1395 (3):315–320; Accession No. Y13804; Accession No. Y10984; Accession No. U22359).

Variants and functional fragments, including shufflents, of the above enzymes, specifically including cystathionine gamma synthase and serine acetyl transferase, may be utilized. It is only required that the enzymes have an activity sufficient to modulate the level of a particular organic sulfur compound in a plant. Variants can be produced by methods known in the art. Variant proteins include those proteins derived from the native protein by deletion (so-called truncation), addition, or substitution of one or more amino acids at one or more sites in the native protein. Additional sequences for use in the invention may be obtained by screening DNA libraries or sequence databases of plants or other species. Some of the RNA partial sequences and precursors listed above may be used to screen DNA libraries to obtain full length genomic or cDNA sequences.

Amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (2d ed., Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

The cystathionine gamma synthase and serine acetyl transferase nucleic acids, as well as any additional genes of interest, can be optimized for enhanced expression in plants of interest. See, for example, EPA0359472; WO91/16432; Perlak et al. (1991) *Proc. Natl. Acad. Sci. USA* 88:3324–3328; and Murray et al. (1989) *Nucleic Acids Res.* 17:477–498. In this manner, the nucleic acids can be synthesized utilizing plant-preferred codons. See, for example, Murray et al. (1989) *Nucleic Acids Res.* 17:477–498, the disclosure of which is incorporated herein by reference. In this manner, synthetic nucleic acids can also be made based on the distribution of codons a particular host uses for a particular amino acid.

Another method for obtaining modified enzymes that can alter the level of at least one organic sulfur compound is by sequence shuffling. Sequence shuffling is described in PCT publication No. 96/19256. See also, Zhang et al. (1997) *Proc. Natl. Acad. Sci. USA* 94:4504–4509. Libraries of recombinant polynucleotides are generated from a population of related sequence polynucleotides comprising sequence regions that have substantial sequence identity and can be homologously recombined in vitro or in vivo.

The terms cystathionine gamma synthase nucleic acid and serine acetyl transferase nucleic acid used in this application refer to all nucleic acids described herein or obtainable by the methods described herein that, when utilized in the present invention, alter the level of an organic sulfur compound.

In some instances, the enzymes of interest are natively expressed in the plant. However, by transformation with heterologous promoters, expression levels or patterns can be altered. See, for example, Sambrook et al. (1989) *Molecular Cloning: A Laboratory Manual* (2d ed., Cold Spring Harbor Laboratory Press, Plainview, N.Y.). and Innis et al. (1990) *PCR Protocols: A Guide to Methods and Applications* (Academic Press, New York).

The nucleic acids can be combined with constitutive or non-seed tissue-specific promoters for expression of the metabolite of interest. Such constitutive promoters include, for example, the core promoter of the Rsyn7 (copending U.S. patent application Ser. No. 08/661,601), the core CaMV 35S promoter (Odell et al. (1985) *Nature* 313: 810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Non-seed tissue specific promoters include, for example Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. All of such promoters can be modified, if necessary, for weak expression.

Leaf-preferred promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

Root-preferred promoters are known and can be selected from the many available from the literature or isolated de novo from various compatible species. See, for example, Hire et al. (1992) *Plant Mol. Biol.* 20(2): 207–218 (soybean root-preferred glutamine synthetase gene); Keller and Baumgartner (1991) *Plant Cell* 3(10):1051–1061 (root-preferred control element in the GRP 1.8 gene of French bean); Sanger et al. (1990) *Plant Mol. Biol.* 14(3):433–443 (root-preferred promoter of the mannopine synthase (MAS) gene of *Agrobacterium tumefaciens*); and Miao et al. (1991) *Plant Cell* 3(1): 11–22 (full-length cDNA clone encoding cytosolic glutamine synthetase (GS), which is expressed in roots and root nodules of soybean). See also Bogusz et al. (1990) *Plant Cell* 2(7):633–641, where two root-preferred promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-preferred promoter activity was preserved. Leach and Aoyagi (1991) describe their analysis of the promoters of the highly expressed ro1C and ro1D root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343–350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4): 759–772); and ro1B promoter (Capana et al. (1994) *Plant Mol. Biol.* 25(4):681–691. See also U.S. Pat. Nos. 5,837,876; 5,750,386; 5,633,363; 5,459,252; 5,401,836; 5,110,732; and 5,023,179. Tissue preferred and specific promoters also include the tissue specific and tissue preferred promoters listed in PCT application publication number WO 00/36124, Page 35, Table A, which table is hereby incorporated by reference.

"Seed-specific" promoters, such as globulin 1, glutelin 2, cruciferin, napin, B-conglycinin, phaseolin, as well as other seed or endosperm specific promoters are not appropriate for use in the present invention.

The promoter may be native or analogous or foreign or heterologous to the plant host. Additionally, the promoter may be a synthetic sequence. By foreign is intended that the transcriptional initiation region is not found in the native plant into which the transcriptional initiation region is introduced. Although both monocot and dicot promoters are described herein, monocot promoters are preferred for use in the present invention.

Expression cassettes will comprise a promoter linked to the coding sequence or antisense sequence of the nucleotide of interest. Such an expression cassette is generally provided with a plurality of restriction sites for insertion of the sequence to be under the transcriptional regulation of the regulatory regions. The expression cassette may additionally contain selectable marker genes.

The transcriptional cassette will include in the 5'-to-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Transformation protocols as well as protocols for introducing nucleotide sequences into plants may vary depending on the type of plant or plant cell targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055); direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The biosynthesis of organic sulfur compounds can be altered in accordance with the present invention in any monocot plant of interest. Of particular interest are plants useful for human and domestic animal food. Such plants include forages and seed crop plants such as cereal crops. Of particular interest are plants where the seed is produced in high amounts, or the seed or a seed part is edible. Seeds of interest include the grain seeds such as wheat, barley, rice, corn, rye, millet and sorghum. Especially preferred plants are corn, wheat and rice.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The following examples are offered by way of illustration and not by way of limitation.

EXAMPLES

EXAMPLE 1

Transformation and Regeneration of Transgenic Maize Plants with Cystathionine Gamma Synthase Immature maize embryos from greenhouse donor plants are bombarded with a plasmid containing cystathionine gamma synthase nucleotide sequence (Accession No. AF007786) operably linked to a ubiquitin promoter (U.S. Pat. Nos. 5,510,474 and 5,614,399) that has been optimized for maize codon preference and a pin II terminator (An et. al. 1989), plus the selectable marker gene PAT (Wohlleben et al. (1988) *Gene* 70:25–37) that confers resistance to the herbicide Bialaphos.

Transformation of Maize

Freshly isolated immature embryos of maize, about 10 days after pollination (DAP), are cultured for 4–5 days before transforming DNA is delivered via particle bombardment. The preferred genotype for transformation is the highly transformable genotype Hi-II (Armstrong, C. L., 1991, Development and Availability of Germplasm with High Type II Culture Formation Response, Maize Genetics Cooperation Newsletter, 65:92–93). An $F_1$ hybrid created by crossing with a Hi-II with an elite inbred may also be used. After DNA delivery, the embryos are cultured on medium containing toxic levels of herbicide. Only those cells which receive the herbicide-resistance gene, and the linked gene(s), grow on selective medium. Transgenic events so selected are propagated and regenerated to whole plants, produce seed, and transmit transgenes to progeny.

Particle Gun Terminology and Use

The PDS-1000 Biolistics particle bombardment device is used to transform maize. The operation of this device is detailed in the operating instructions available from the manufacturer (Bio-Rad Laboratories, Hercules, Calif.).

The macrocarrier flight distance is fixed in the instrument at ¼" (0.25"). While the rupture disk-macrocarrier gap distance is adjustable, the device is operated at the factory recommended distance of ⅛" (0.125").

Preparation of Particles

The transforming DNA is associated with either tungsten or gold particles. Prior to association with the transforming DNA, the tungsten particles are prepared essentially as described by Tomes et al. U.S. Pat. No. 5,990,387).

The preferred method utilizes gold particles. Gold particles are prepared as follows. Sixty mg of 0.6µ gold particles (Bio-Rad) are placed in 2.0 mL Sarstedt tube. The particles are washed three times in absolute ethanol (100%). Each ethanol wash involves adding one mL of absolute ethanol to the tube, sonicating the tube briefly, vortexing the tube on high for one minute, centrifuging the tube to pellet the particles and discarding the supernatant. The particles are then washed two times in sterile deionized water. Each wash involves adding one mL of sterile deionized water to the tube, sonicating the tube briefly, vortexing the tube on high for one minute, centrifuging the tube to pellet the particles and discarding the supernatant. Following the ethanol and water wash steps, one mL of sterile deionized water is added to the tube and the tube is sonicated. Aliquots (250 μL) of the particle-containing suspension are removed to siliconized 1.5 mL tubes and combined with 750 μL sterile deionized water.

Association of Particles with Transforming DNA

The transforming DNA is associated with the prepared tungsten or gold particles by precipitation in a solution comprising $CaCl_2$ and spermidine as follows. A tube containing tungsten or gold particles prepared as described above is sonicated for 3 seconds at setting 2.5 in a water bath probe, Branson Sonicator #450 (Branson Ultrasonics Corp., Danbury Conn.). Ten μL plasmid DNA (1 μg plasmid total) in TE buffer is added to the tube and mixed for 5 seconds. Next, 100 μL 2.5 M $CaCl_2$ and 10 μL 0.1 M spermidine are added. The tube is then shaken on a vortexer for 10 minutes followed by centrifugation for 30 seconds at 10,000 rpm. The supernatant is removed and discarded, and 500 μL absolute ethanol is added. The tube is then sonicated at setting 2.5 for 3 seconds, centrifuged for 30 seconds at 10,000 rpm and the supernatant removed. To the tube, 105 μL of absolute ethanol is added. The tube is sonicated for 3 seconds at setting 2.5 before placing a 10 μL aliquot onto the center of a macrocarrier.

Preparation of Target Tissue

Ears of Hi-II or Hi-II X elite inbred are sampled in planta to assess the developmental stage of the embryos. When immature embryos first become opaque, about 9–12 days post-pollination, the ears are harvested for embryo dissection. The embryos are approximately 1.5–1.8 mm long from coleoptilar to coleorhizal end. Immature embryos are the target tissue for transient and stable transformation experiments.

The ears are surface sterilized in 50% (λ/λ) Clorox bleach+0.5% (λ/λ) Micro detergent for 20 minutes, and then rinsed twice with sterile water. The immature embryos are excised from the caryopsis and placed embryo axis side down (scutellum side up) onto transformation support medium.

Embryos are cultured on 560 L medium for 4–5 days in darkness at 28° C. At this time, a small amount of incipient embryogenic tissue can be observed at the coleorhizal end of the scutellum, but there is no production of subculturable tissue.

Delivery of DNA

As preparation for bombardment, the 4 day pre-cultured embryos are transferred to 561Y medium, which contains elevated sucrose, and are incubated in darkness at 28° C. for 4 hours. The embryos are arranged, 10 embryos per plate, in a 2 cm target area. The embryos are angled with their coleorhizal end pointing up toward the macrocarrier at approximately a 30° angle. This orientation of the cultured embryos enhances exposure of the preferred cell targets to the path of particles propelled by the particle gun.

Plates of embryos are bombarded at shelf 2 from the bottom of the device, 650 PSI rupture disk, and a chamber vacuum of 28 mm Hg.

The bombarded plates are incubated in darkness at 28° C. for two days. After the two-day bombardment recovery period, the embryos are transferred to Petri dishes containing 560 R medium. This latter medium is comprised of those components which typically are used to initiate and promote embryogenic tissue from maize embryos, and contains 2% sucrose, and 3 ppm bialaphos as a selective agent. The plates are incubated in darkness at 28° C. for 4–6 weeks, or until growth of putatively transformed events are observed. 560 R culture medium does not support the growth of untransformed tissue derived from the bombarded embryos. Therefore, only putatively transformed tissue, resistant to bialaphos as a consequence of expressing the resistance transgene, are competent to grow.

Putatively transformed events are identified first by their growth under selective conditions and individually subcultured to fresh 560 R medium for propagation. Samples of each event are assayed for their transgenic nature by PCR reaction using primer sets designed to specifically amplify sequences in the inserted gene(s).

Regeneration of $T_0$ Plants

Transformed, selection-resistant embryogenic tissue is transferred to 288 J medium to initiate plant regeneration. Following somatic embryo maturation (2–4 weeks), well-developed somatic embryos are transferred to medium for germination (272 V) and transferred to a lighted culture room. Approximately 7–10 days later, developing plantlets are transferred to 272 V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to 1.6 gallon pots and grown to maturity. Plants are monitored and scored for altered cystathionine gamma synthase and/or phenotype such as increased sulfur compounds.

Media Recipes

Medium 288 J contains the following ingredients: 950.000 ml of D-I $H_2O$; 4.300 g of MS Salts; 0.100 g of Myo-Inositol; 5.000 ml of MS Vitamins Stock Solution (No. 36J); 1.000 ml of Zeatin .5 mg/ml; 60.000 g of Sucrose; 3.000 g of Gelrite, which is added after Q.S. to volume; 2.000 ml of IAA 0.5 mg/ml #; 1.000 ml of 0.1 Mm ABA #; 3.000 ml of Bialaphos 1 mg/ml #; and 2.000 ml of Agribio Carbenicillin 50 mg/ml #. Directions are: dissolve ingredients in polished D-I $H_2O$ in sequence; adjust to pH 5.6; Q.S. to volume with polished D-I $H_2O$ after adjusting pH; sterilize and cool to 60° C. Add 3.5 g/L of Gelrite for cell biology. Ingredients designated with # are added after sterilizing and cooling to temperature.

Medium 272 V contains the following ingredients: 950.000 ml of D-I $H_2O$; 4.300 g of MS Salts; 0.100 g of Myo-Inositol; 5.000 ml of MS Vitamins Stock Solution; 40.000 g of Sucrose; and 6.000 g of Bactoagar, which is added after Q.S. to volume. Directions are: dissolve ingredients in polished D-I $H_2O$ in sequence; adjust to pH 5.6; Q.S. to volume with polished D-I $H_2O$ after adjusting pH; and sterilize and cool to 60° C.

Medium 560 L contains the following ingredients: 950.000 ml of D-I Water, Filtered; 4.000 g of CHU (N6) Basal Salts (SIGMA C-1416); 1.000 ml of Eriksson's Vitamin Mix (1000X SIGMA-1511); 1.250 ml of Thiamine.HCL 0.4 mg/ml; 30.000 g of Sucrose; 4.000 ml of 2,4-D 0.5 mg/ml; 3.000 g of Gelrite, which is added after Q.S. to volume; and 0.425 ml of Silver Nitrate 2 mg/ml #. Directions are: dissolve ingredients in D-I H$_2$O in sequence; adjust to pH 5.8 with KOH; bring up to volume with D-I H$_2$O; sterilize and cool to room temp. Total volume (L)=1.00. Ingredients designated with # are added after sterilizing and cooling to temperature.

Medium 560 R contains the following ingredients: 950.000 ml D-I Water, Filtered; 4.000 g of CHU (N6) Basal Salts (SIGMA C-1416); 1.000 ml Eriksson's Vitamin Mix (1000X SIGMA-1511); 1.250 ml of Thiamine.HCL 0.4 mg/ml; 30.000 g Sucrose; 4.000 ml of 2,4-D 0.5 mg/ml; 3.000 g of Gelrite, which is added after Q.S. to volume; 0.425 ml of Silver Nitrate 2 mg/ml #; and 3.000 ml of Bialaphos 1 mg/ml #. Directions are: dissolve ingredients in D-I H$_2$O in sequence; adjust to pH 5.8 with KOH; bring up to volume with D-I H$_2$O; sterilize and cool to room temp. Total volume (L)=1.00. Ingredients designated with # are added after sterilizing and cooling to temperature.

Medium 561 Y contains the following ingredients: 950.000 ml of D-I Water, Filtered; 4.000 g of CHU (N6) Basal Salts (SIGMA C-1416); 1.000 ml of Eriksson's Vitamin Mix (1000X SIGMA-1511); 1.250 ml of Thiamine.HCL 0.4 mg/ml; 190.000 g of Sucrose; 2.000 ml of 2,4-D 0.5 mg/ml; 2.880 g of L-Proline; 2.000 g of Gelrite, which is added after Q.S. to volume; and 4.250 ml of Silver Nitrate 2 mg/ml #. Directions are: dissolve ingredients in D-I H$_2$O in sequence; adjust to pH 5.8 with KOH; bring up to volume with D-I H$_2$O; sterilize and cool to room temp. Autoclave less time because of increased sucrose. Total volume (L)=1.00. Ingredients designated with # are added after sterilizing and cooling to temperature.

EXAMPLE 2

*Agrobacterium*-mediated Transformation of Maize with Cystathionine Gamma Synthase For *Agrobacterium*-mediated transformation of maize with a cystathionine gamma synthase nucleotide sequence, a maize cDNA for cystathionine gamma synthase (Accession No. AF007786) is fused to a maize optimized ubiquitin promoter (U.S. Pat. Nos. 5,510,474 and 5,614,399) that has been optimized for maize codon preference and a pin II terminator sequence (An, et al., 1989). The cystathionine gamma synthase cassette, also containing a CaMV35S—bialaphos selectable marker element, is cloned into a binary vector and introduced into *Agrobacterium*.

Transformation of Maize Mediated by *Agrobacterium*

Freshly isolated immature embryos of maize, about 10 days after pollination (DAP), are incubated with the *Agrobacterium*. The preferred genotype for transformation is the highly transformable genotype Hi-II (Armstrong, C. L., 1991, Development and Availability of Germplasm with High Type II Culture Formation Response, Maize Genetics Cooperation Newsletter, 65:92–93). An F$_1$ hybrid created by crossing with an Hi-II with an elite inbred may also be used. After *Agrobacterium* treatment of immature embryos, the embryos are cultured on medium containing toxic levels of herbicide. Only those cells which receive the herbicide-resistance gene, and the linked gene(s), grow on selective medium. Transgenic events so selected are propagated and regenerated to whole plants, produce seed, and transmit transgenes to progeny.

Preparation of Agrobacterium

The engineered *Agrobacterium tumefaciens* LBA4404 is constructed as per U.S. Pat. No. 5,591,616 to contain the linked gene(s) and the selectable marker gene. Typically either BAR (D'Halluin et al. (1992) *Methods Enzymol* 216:415–426) or PAT (Wohlleben et al. (1988) *Gene* 70:25–37) may be used.

To use the engineered vector in plant transformation, a master plate of single bacterial colonies is first prepared by inoculating the bacteria on minimal AB medium and then incubating the bacteria plate inverted at 28° C. in darkness for about 3 days. A working plate is then prepared by selecting a single colony from the plate of minimal A medium and streaking it across a plate of YP medium. The YP-medium bacterial plate is then incubated inverted at 28° C. in darkness for 1–2 days.

*Agrobacterium* for plant transfection and co-cultivation is prepared 1 day prior to transformation. Into 30 ml of minimal A medium in a flask is placed 50 µg/ml spectinomycin (or appropriate bacterial antibiotic depending on marker in co-integrate), 100 µM acetosyringone, and about a ⅛ loopful of *Agrobacterium* from a 1 to 2-day-old working plate. The *Agrobacterium* is then grown at 28° C. at 200 rpm in darkness overnight (about 14 hours). In mid-log phase, the *Agrobacterium* is harvested and resuspended at 3 to 5×10$^8$ CFU/ml in 561Q medium+100 µM acetosyringone using standard microbial techniques and standard curves.

Immature Embryo Preparation

Nine to ten days after controlled pollination of a corn plant, developing immature embryos are opaque and 1–1.5 mm long and are the appropriate size for Agro-infection. The husked ears are sterilized in 50% commercial bleach and 1 drop Tween for 30 minutes, and then rinsed twice with sterile water. The immature embryos are aseptically removed from the caryopsis and placed into 2 ml of sterile holding solution comprising of 561Q+100 µM acetosyringone.

*Agrobacterium* Infection and Co-cultivation of Embryos

Holding solution is decanted from excised immature embryos and replaced with prepared *Agrobacterium*. Following gentle mixing and incubation for about 5 minutes, the *Agrobacterium* is decanted from the immature embryos. Immature embryos are then moved to a plate of 562P medium, scutellum surface upwards, and incubated at 20° C. for 3 days in darkness followed by incubation at 28° C. for 3 days in darkness on medium 562P+100 mg/ml carbenecillin (see U.S. Pat. No. 5,981,840).

Selection of Transgenic Events

Following incubation, the immature embryos are transferred to 5630 medium for selection of events. The transforming DNA possesses a herbicide-resistance gene, in this example the PAT gene, which confers resistance to bialaphos. At 10- to 14-day intervals, embryos are transferred to 5630 medium. Actively growing putative transgenic embryogenic tissue are visible in 6–8 weeks.

Regeneration of T$_0$ Plants

Transgenic embryogenic tissue is transferred to 288W medium and incubated at 28° C. in darkness until somatic embryos matured, or about 10 to 18 days. Individual matured somatic embryos with well-defined scutellum and coleoptile are transferred to 272 embryo germination medium and incubated at 28° C. in the light. After shoots and roots emerge, individual plants are potted in soil and hardened-off using typical horticultural methods.

Confirmation of Transformation

Putative transgenic events are subjected to analysis to confirm their transgenic nature.

Events are tested for the presence of the cystathionine gamma synthase by PCR amplification. Additionally, $T_0$ plants are painted with bialaphos herbicide. The subsequent lack of a herbicide-injury lesion indicates the presence and action of the herbicide resistance gene. The plants are monitored and scored for altered cystathionine gamma synthase expression and/or phenotype such as increased organic sulfur compounds.

Media Recipes

Medium 561 Q contains the following ingredients: 950.000 ml of D-I Water, Filtered; 4.000 g of Chu (N6) Basal Salts (Sigma C-1416); 1.000 ml of Eriksson's Vitamin Mix (1000x Sigma-1511); 1.250 ml of Thiamine.HCL.4 mg/ml; 3.000 ml of 2,4-D 0.5 mg/ml (No. 2A); 0.690 g of L-proline; 68.500 g of Sucrose; and 36.000 g of Glucose. Directions are: dissolve ingredients in polished D-I $H_2O$ in sequence; adjust pH to 5.2 w/KOH; Q.S. to volume with polished D-I $H_2O$ after adjusting pH; and filter sterilize (do not autoclave).

Medium 562 P contains the following ingredients: 950.000 ml of D-I Water, Filtered; 4.000 g of Chu (N6) Basal Salts (Sigma C-1416); 1.000 ml of Eriksson's Vitamin Mix (1000x Sigma-1511); 1.250 ml of Thiamine.HCL.4 mg/ml; 4.000 ml of 2,4-D 0.5 mg/ml; 0.690 g of L-proline; 30.000 g of Sucrose; 3.000 g of Gelrite, which is added after Q.S. to volume; 0.425 ml of Silver Nitrate 2 mg/ml #; and 1.000 ml of Aceto Syringone 100 mM #. Directions are: dissolve ingredients in polished D-I $H_2O$ in sequence; adjust pH to 5.8 w/KOH; Q.S. to volume with polished D-I $H_2O$ after adjusting pH; and sterilize and cool to 60° C. Ingredients designated with a # are added after sterilizing and cooling to temperature.

Medium 563 O contains the following ingredients: 950.000 ml of D-I Water, Filtered; 4.000 g of Chu (N6) Basal Salts (Sigma C-1416); 1.000 ml of Eriksson's Vitamin Mix (1000x Sigma-1511); 1.250 ml of Thiamine.HCL.4 mg/ml; 30.000 g of Sucrose; 3.000 ml of 2,4-D 0.5 mg/ml (No. 2A); 0.690 g of L-proline; 0.500 g of Mes Buffer; 8.000 g of Agar (Sigma A-7049, Purified), which is added after Q.S. to volume; 0.425 ml of Silver Nitrate 2 mg/ml #; 3.000 ml of Bialaphos 1 mg/ml #; and 2.000 ml of Agribio Carbenicillin 50 mg/ml #. Directions are: dissolve ingredients in polished D-I $H_2O$ in sequence; adjust to pH 5.8 w/koh; Q.S. to volume with polished D-I $H_2O$ after adjusting pH; sterilize and cool to 60° C. Ingredients designated with a # are added after sterilizing and cooling to temperature.

Medium 288 W contains the following ingredients: 950.000 ml of D-I $H_2O$; 4.300 g of MS Salts; 0.100 g of Myo-Inositol; 5.000 ml of MS Vitamins Stock Solution (No. 36J); 1.000 ml of Zeatin.5 mg/ml; 60.000 g of Sucrose; 8.000 g of Agar (Sigma A-7049, Purified), which is added after Q.S. to volume; 2.000 ml of IAA 0.5 mg/ml #; 1.000 ml of 0.1 Mm ABA #; 3.000 ml of Bialaphos 1 mg/ml #; and 2.000 ml of Agribio Carbenicillin 50 mg/ml #. Directions are: dissolve ingredients in polished D-I $H_2O$ in sequence; adjust to pH 5.6; Q.S. to volume with polished D-I $H_2O$ after adjusting pH; sterilize and cool to 60° C. Add 3.5 g/L of Gelrite for cell biology. Ingredients designated with a # are added after sterilizing and cooling to temperature.

Medium 272 contains the following ingredients: 950.000 ml of D-I $H_2O$; 4.300 g of MS Salts; 0.100 g of Myo-Inositol; 5.000 of MS Vitamins Stock Solution; 40.000 g of Sucrose; and 1.500 g of Gelrite, which is added after Q.S. to volume. Directions are: dissolve ingredients in polished D-I $H_2O$ in sequence; adjust to pH 5.6; Q.S. to volume with polished D-I $H_2O$ after adjusting pH; and sterilize and cool to 60° C.

Medium minimal A contains the following ingredients: 950.000 ml of D-I $H_2O$; 10.500 g of potassium phosphate dibasic K2HPO4; 4.500 g of potassium phosphate monobasic KH2PO4; 1.000 g of ammonium sulfate; 0.500 g of sodium citrate dihydrate; 10.000 ml of sucrose 20% solution #; and 1.000 ml of IM magnesium sulfate #. Directions are: dissolve ingredients in polished D-I $H_2O$ in sequence; Q.S. to volume with D-I $H_2O$; sterilize and cool to 60° C. Ingredients designated with a # are added after sterilizing and cooling to temperature.

Medium minimal AB contains the following ingredients: 850.000 ml of D-I $H_2O$; 50.000 ml of stock solution 800A; 9 g of Phytagar which is added after Q.S. to volume; 50.000 ml of stock solution 800B #; 5.000 g of glucose #; and 2.000 ml of spectinomycin 50/mg/ml stock #. Directions are: dissolve ingredients in polished D-I $H_2O$ in sequence; Q.S. to volume with polished D-I $H_2O$ less 100 ml per liter; sterilize and cool to 60° C. Ingredients designated with a # are added after sterilizing and cooling to temperature. Stock solution 800A contains the following ingredients: 950.000 ml of D-I $H_2O$; 60.000 g of potassium phosphate dibasic K2HPO4; and 20.000 g of sodium phos. monobasic, hydrous. Directions are: dissolve ingredients in polished D-I $H_2O$ in sequence; adjust pH to 7.0 w/koh; Q.S. to volume with polished D-I $H_2O$ after adjusting pH; and sterilize and cool to 60° C. Stock solution 800B contains the following ingredients: 950.000 ml of D-I $H_2O$; 20.000 g of ammonium chloride; 6.000 g of magnesium sulfate 7-$H_2O$, MgSO4, 7$H_2O$; 3.000 g of potassium chloride; 0.200 g of calcium chloride (anhydrate); and 0.050 g of ferrous sulfate 7-hydrate. Directions are: dissolve ingredients in polished D-I $H_2O$ in sequence; Q.S. to volume with polished D-I B20; and sterilize and cool to 60° C.

Medium minimal YP contains the following ingredients: 950.000 ml of D-I $H_2O$; 5.000 g of yeast extract (Difco); 10.000 g of peptone (Difco); 5.000 g of sodium chloride; 15.000 g of bacto-agar, which is added after Q.S. to volume; and 1.000 ml of spectinomycin 50 mg/ml stock #. Directions are: dissolve ingredients in polished D-I 1$H_2O$ in sequence; adjust pH to 6.8 w/koh; Q.S. to volume with polished D-I $H_2O$ after adjusting pH; sterilize and cool to 60° C. Ingredients designated with a # are added after sterilizing and cooling to temperature.

Results

Figure 2:
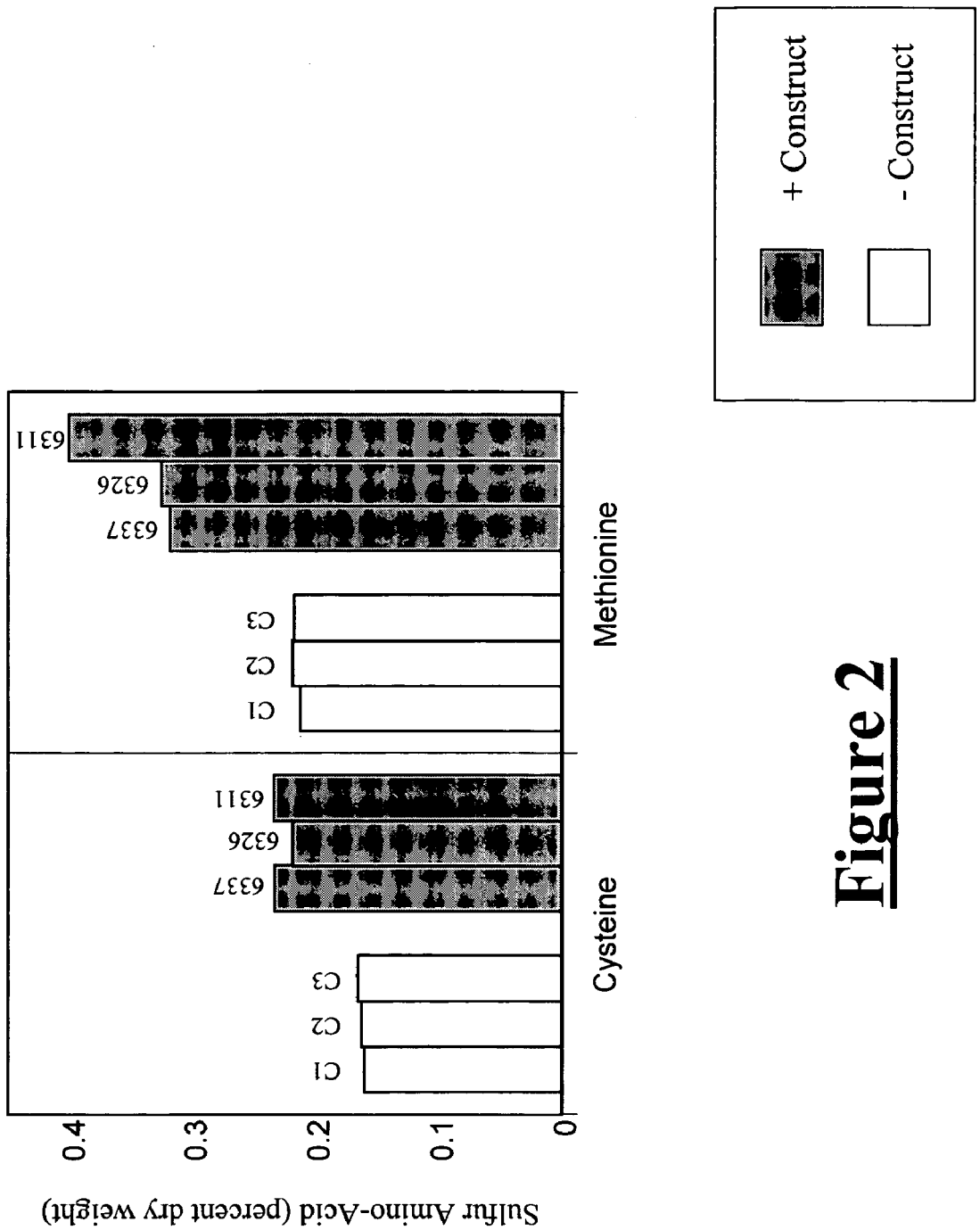
FIG. 2 sets forth the sulfur amino acid level, on a percent dry weight basis, of certain cystathionine gamma synthase transformed lines.

Following two generations of selfing, plants homozygous for the cystathionine gamma synthase construct and null segregates derived from more than 40 events are analyzed. As can be seen in FIG. 2, forty seeds from each of three events homozygous for cystathionine gamma synthase (6337, 6326, 6311; shown by shaded bars on FIGS. 2 and 3) and null segregants (C1–C3; shown by open bars on FIGS. 2 and 3) are analyzed for total sulfur content of amino acids. (Beckman Instruments 6300 analyzer—amino acids detected with ninhydrin.) Events homozygous for cystathionine gamma synthase show a statistically significant increase in levels of cysteine and methionine over the null segregates. The cysteine and methionine levels in the homozygous events greatly surpass any increase previously achieved through enzymatic modification with a 38% increase in cysteine on a dry weight basis and a 49% increased in methionine on a dry weight basis (FIG. 2).

Figure 3:
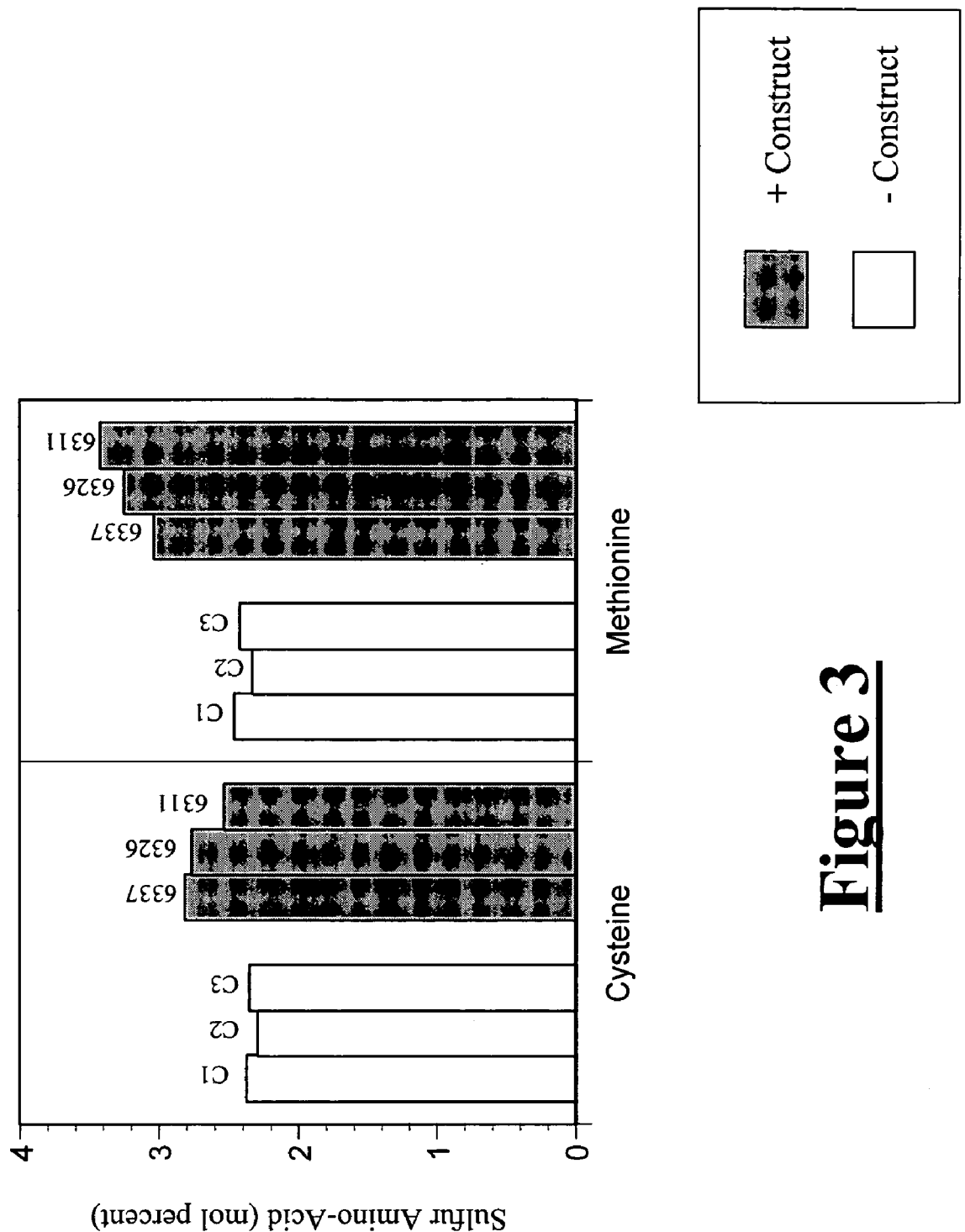
FIG. 3 sets forth the sulfur amino acid level, on a mol percent level, of certain cystathionine gamma synthase transformed lines.

As can be seen in FIG. 3, when expressed on a mol percent basis, the data shows that the concentration of cysteine has increased by 9% and methionine has increased by 20%, each of which is statistically significant at a p value of less than 0.05. Over expression of cystathionine gamma synthase in transgenic lines was also confirmed by western blot analysis. Thus, Applicants show that constitutive expression of cystathionine gamma synthase leads to substantial and unexpected increases in total seed cysteine and methionine levels.

EXAMPLE 3

Transformation and Regeneration of Transgenic Maize Callus with Serine Acetyl Transferase Immature maize embryos from greenhouse donor plants are bombarded with a plasmid containing serine acetyl transferase nucleotide sequence (Seq. ID No. 1) operably linked to a ubiquitin promoter (U.S. Pat. Nos. 5,510,474 and 5,614,399) that has been optimized for maize codon preference and a pin II terminator (An et. al. 1989), plus a plasmid containing the selectable marker gene PAT (Wohlleben et al. (1988) *Gene* 70:25–37) that confers resistance to the herbicide Bialaphos. Transformation is performed according to the procedure described in Example 1.

EXAMPLE 4

*Agrobacterium*-mediated Transformation of Maize with Serine Acetyl Transferase

For *Agrobacterium*-mediated transformation of maize with a serine acetyl transferase nucleotide sequence, a maize cDNA for serine acetyl transferase (Sequence ID No. 1) is fused to a ubiquitin promoter sequence (U.S. Pat. Nos. 5,510,474 and 5,617,399) that has been optimized for maize codon preference and a pin II terminator sequence (An, et al., 1989). The serine acetyl transferase cassette, also contains a CaMV35S—bialaphos selectable marker element, is cloned into a binary vector and introduced into *Agrobacterium*. Transformation is performed according to the procedure described in Example 2.

EXAMPLE 5

*Agrobacterium*-Mediated Transformation of Maize with Serine Acetyl Transferase and ATP Sulfurylase Transgenic plants are constructed by Applicants according to the method described in Example 4, but with an expression cassette containing both the serine acetyl transferase sequence described in Example 4 and an ATP Sulfurylase sequence (Sequence ID No. 3) linked to a ubiquitin promoter sequence (U.S. Pat. Nos. 5,510,474 and 5,617, 399) that has been optimized for maize codon preference and a Pin II terminator sequence (An, et al., 1989).

Results

Figure 4:
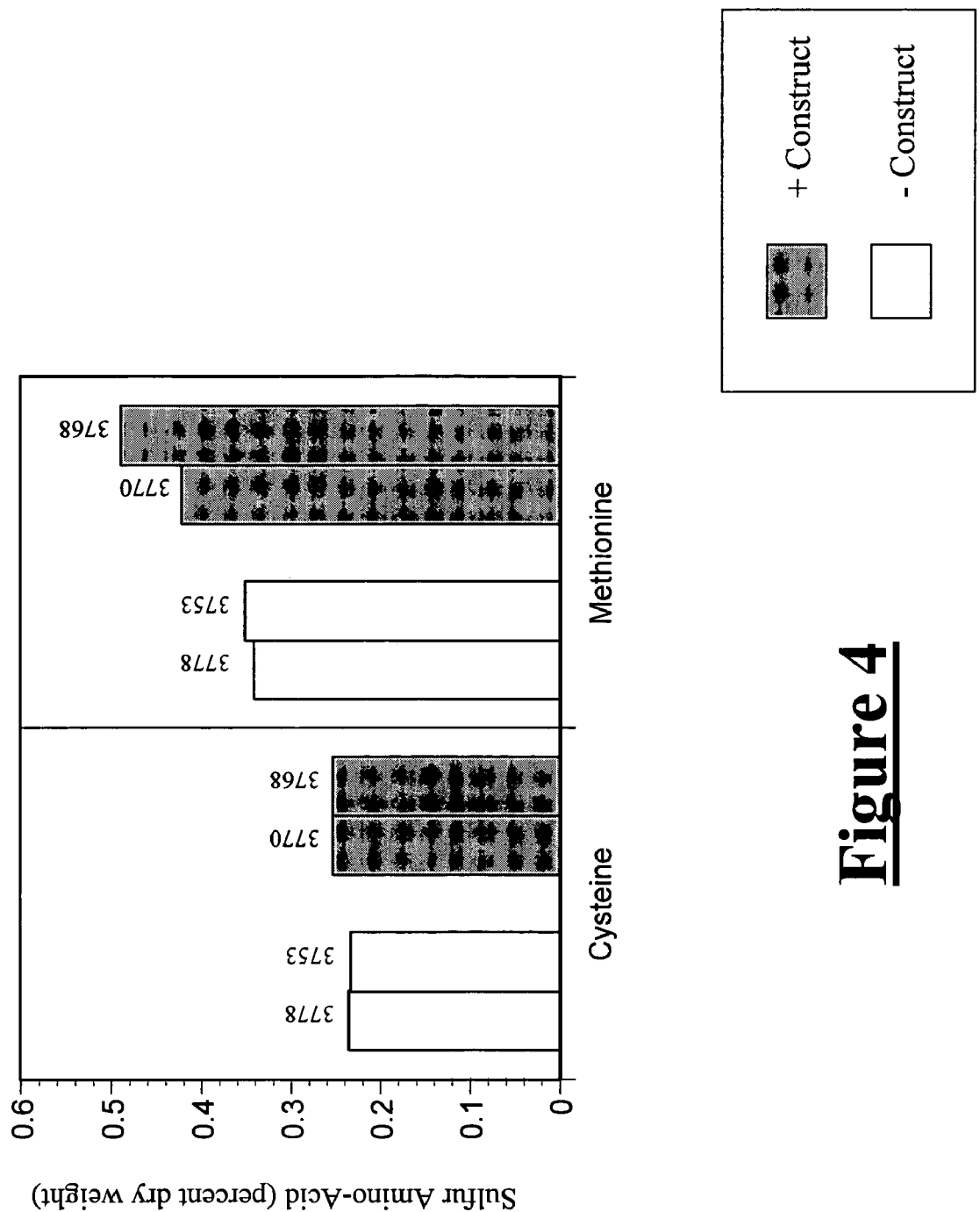
FIG. 4 sets forth the sulfur amino acid level, on a percent dry weight basis, of certain serine acetyl transferase transformed lines.
Figure 5:
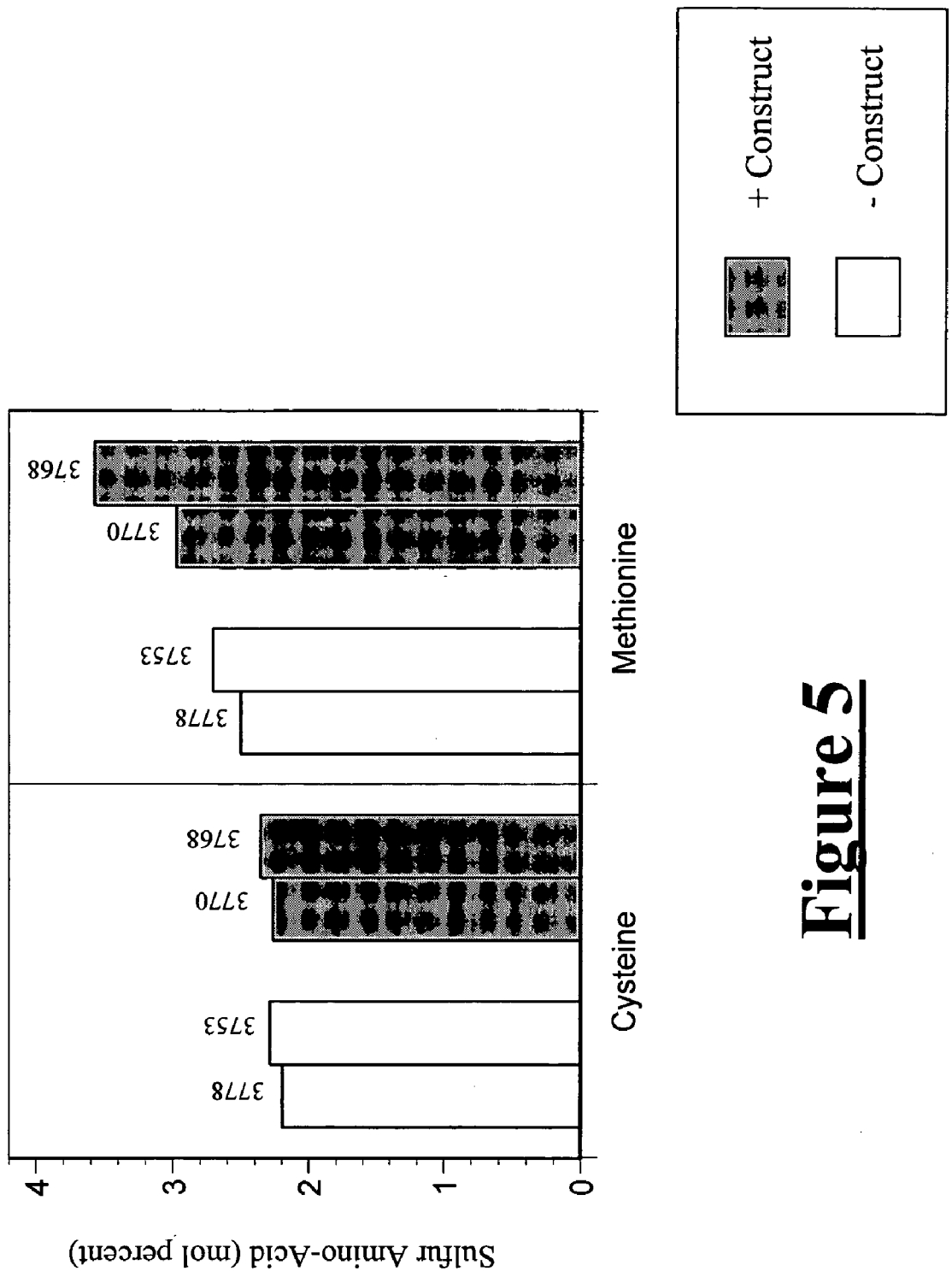
FIG. 5 sets for the sulfur amino acid level, on a mol percent level, of certain serine acetyl transferase transformed lines.

More than twenty events producing T1 seed are analyzed for overexpression of both genes by western blot analysis. Twenty to forty seeds from each of two events show strong expression of both ATP Sulfurylase and serine acetyl transferase, and two events showing weak or undetectable expression are analyzed for total sulfur amino acid content (Beckman Instruments 6300 analyzer—amino acids detected with ninhydrin). These results are shown in FIGS. 4 and 5. Samples 3770 and 3768 (represented by the shaded bars in FIGS. 4 and 5) showed strong expression of ATP Sulfurylase and serine acetyl transferase, while samples 3778 and 3753 (represented by the open bars in FIGS. 4 and 5) showed weak expression of ATP Sulfurylase and serine acetyl transferase. Segregating seed from event 3768 is propagated, selfed, and the plants are analyzed for the presence of the construct by their resistance to herbicide. T2 (second generation) seed was harvested from both resistant and susceptible plants. Sulfur amino acids were analyzed for total sulfur amino acid content using a Beckman Instruments 6300 analyzer, with the amino acids detected by ninhydrin. Results are shown in FIGS. 6 and 7 with the herbicide resistant lines (+construct) represented by shaded bars and the herbicide susceptible lines (−construct) represented by open bars.

Figure 6:
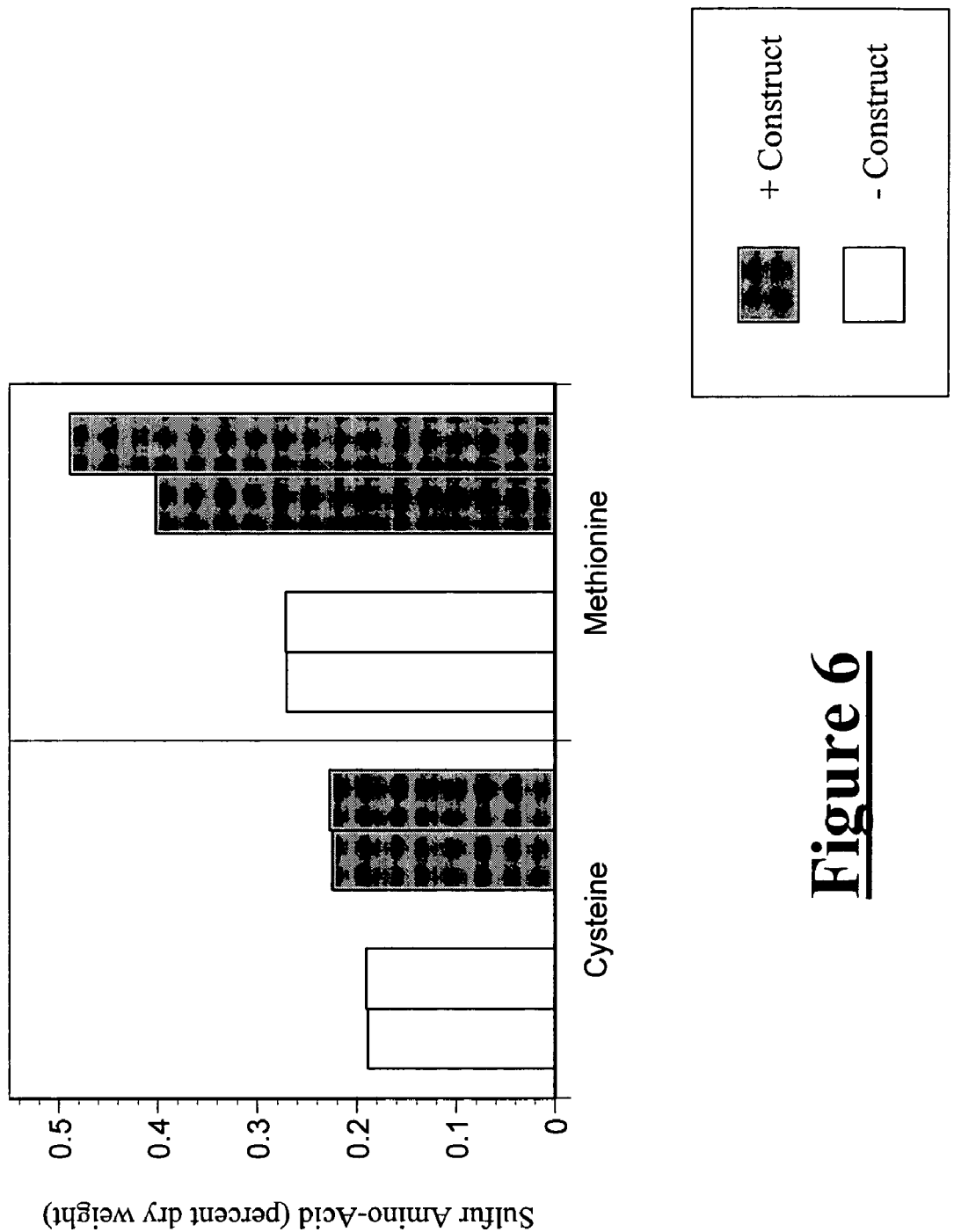
FIG. 6 sets for the sulfur amino acid level, on a percent dry weight basis, of the segregating seed (T2) of certain serine acetyl transferase transformed lines.
Figure 7:
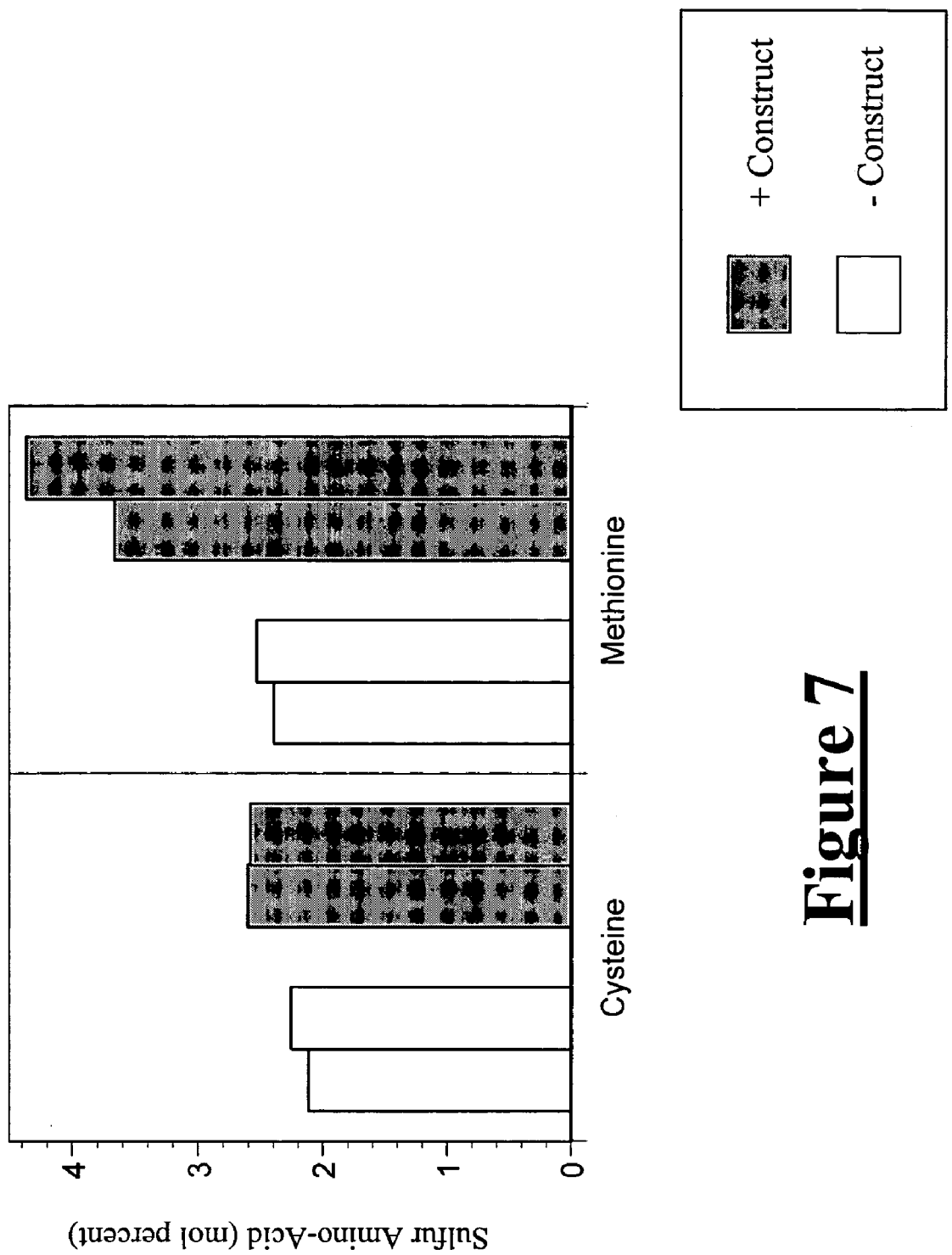
FIG. 7 sets for the sulfur amino acid level, on a mol percent level dry weight basis, of the segregating seed (T2) of certain serine acetyl transferase transformed lines.

The cysteine and methionine levels in the plants with serine acetyl transferase and ATP Sulfurylase greatly surpassed any increase previously achieved through enzymatic modification with a 20% average increase in cysteine on a dry weight basis and a 97% average increase in methionine on a dry weight basis (FIG. 6). As can be seen in FIG. 7, when expressed on a mol percent basis, the data shows that the concentration of cysteine has increased by an average of 19% and methionine has increased by an average of 63%. Although the construct used by Applicants contains both serine acetyl transferase and ATP Sulfurylase, Applicant believes that the increase in the cysteine and methionine levels of the transformed plants is due to the serine acetyl transferase rather than the ATP Sulfurylase. Thus, the preferred embodiment is the construct taught herein that comprises only the serine acetyl transferase nucleic acid and not the ATP Sulfurylase nucleic acid. However, the data demonstrates that a construct with both the serine acetyl transferase nucleic acid and the ATP Sulfurylase nucleic acid may be used to modulate the biosynthesis of at least one organic sulfur compound. Similarly, only the ATP Sulfurylase nucleic acid and not the serine acetyl transferase nucleic may also be used to modulate the biosynthesis of at least one organic sulfur compound. Such constructs, and plants with such constructs, may be produced by the methods taught in the Examples described herein.

Although Applicant has taught examples using specific enzymes that it believes to be preferred for use in the present invention, Applicant has more generally taught that, to increase sulfur amino acids and organic sulfur compounds via enzymatic modification in the seed of a monocot plant, it is sufficient to express such enzymes in the non-seed tissue of the monocot plant. The plant will then translocate these sulfur amino acids and organic sulfur compounds to the seed, where the seed, without any genetic modification, will accumulate such amino acids and compounds. Applicant reasonably believes that any one or more of the enzymes along the sulfate/serine to cysteine pathways (FIG. 1) will function in the manner as taught herein. In such case, a construct may be produced in the manner described herein but using such enzyme or enzymes. One or more enzymes in the sulfate to cysteine and/or the serine to cysteine pathways are referred to herein as "sulfur assimilating enzymes." Such term also includes additional enzymes that may activate or deactivate such enzymes, such as kinases that activate or inactivate such enzymes by phosphorylation.

In summary, Applicant has shown that constitutive or non-seed expression of one or more enzymes in the cysteine biosynthetic pathway leads to substantial and unexpected increases in total seed cysteine and methionine levels. This increase in cysteine and methionine can be utilized as a sulfur source for the production of other organic sulfur compounds. Subsequent production of the other organic sulfur compounds from this increased sulfur source may occur in either the seed, leaf, root, stem or other plant tissue.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for modulating biosynthesis of at least one organic sulfur compound in the seed of a monocotyledonous plant, the method comprising stably transforming the plant with a DNA construct comprising the nucleic acid sequence of SEQ ID NO: 1, wherein the nucleic acid is operably linked to a non-seed specific promoter that drives expression in the plant and wherein the level of the at least one organic sulfur compound is altered.

2. The method of claim 1, wherein the promoter is ubiquitin.

3. The method of claim 1, wherein the promoter is a tissue-specific promoter for a tissue other than seed.

4. The method of claim 3, wherein the promoter is a root preferred promoter or a leaf-preferred promoter.

5. The method of claim 1, further comprising transforming the plant with a second DNA construct comprising the nucleic acid sequence of SEQ ID NO:3 wherein the nucleic acid sequence in said second DNA construct is operably linked to a promoter that drives expression in the plant.

6. The method of claim 1, wherein the organic sulfur compound is cysteine or methionine.

7. A monoctyledonous plant with seed having increased levels of at least one organic sulfur compound produced by the method of claim 1.

8. The plant of claim 7, wherein the promoter is ubiquitin.

9. The plant of claim 7, wherein the promoter is a tissue-specific promoter for a tissue other than seed.

10. The plant of claim 9, wherein the promoter is a root-preferred promoter or a leaf-preferred promoter.

11. The plant of claim 7, further comprising a second DNA construct comprising a nucleic acid sequence encoding the enzyme of SEQ ID NO:4, functional in the biosynthesis of a selected organic sulfur compound, wherein the nucleic acid sequence is operably linked to a promoter that drives expression in the plant.

12. The plant of claim 7, wherein the organic sulfur compound is cysteine or methionine.

13. The plant of claim 7, wherein said monocotyledonous plant is selected from the group consisting of maize, wheat, barley, rye, rice, millet and sorghum.

14. The plant of claim 13, wherein the plant is maize.

15. A transgenic seed of the plant of claim 7, 13 or 14.

* * * * *